US009775929B2

(12) United States Patent
Behrens et al.

(10) Patent No.: US 9,775,929 B2
(45) Date of Patent: Oct. 3, 2017

(54) SOLUTION BLOW SPUN POLYMER FIBERS, POLYMER BLENDS THEREFOR AND METHODS AND USE THEREOF

(71) Applicants: University of Maryland, College Park, College Park, MD (US); Children's National Medical Center, Washington, DC (US)

(72) Inventors: Adam Behrens, Olney, MD (US); Peter Kofinas, Bethesda, MD (US); Michael Sikorski, Ellicott City, MD (US); Anthony Sandler, Bethesda, MD (US); Priya Srinivasan, Silver Spring, MD (US); Nora Lee, Arlington, VA (US)

(73) Assignees: University of Maryland College Park, College Park, MD (US); Children's National Medical Center, Washington, DC (US)

( * ) Notice: Subject to any disclaimer, the term of this patent is extended or adjusted under 35 U.S.C. 154(b) by 81 days.

(21) Appl. No.: 14/685,175

(22) Filed: Apr. 13, 2015

(65) Prior Publication Data
US 2015/0290356 A1 Oct. 15, 2015

Related U.S. Application Data

(60) Provisional application No. 61/979,054, filed on Apr. 14, 2014, provisional application No. 62/026,073, (Continued)

(51) Int. Cl.
*A61L 24/00* (2006.01)
*A61L 24/04* (2006.01)
(Continued)

(52) U.S. Cl.
CPC ........ *A61L 24/043* (2013.01); *A61L 24/0015* (2013.01); *A61L 27/26* (2013.01); *A61L 27/54* (2013.01)

(58) Field of Classification Search
CPC .................................................... A61L 24/00
See application file for complete search history.

(56) References Cited

U.S. PATENT DOCUMENTS 5,511,960 A    4/1996 Terakawa et al.
5,766,523 A    6/1998 Rodgers et al.
(Continued)

FOREIGN PATENT DOCUMENTS

CN    103266419 A  *  8/2013
WO    WO 2006/002365    1/2006
(Continued)

OTHER PUBLICATIONS

Abu Hilal, M. et al. (2010) "Bleeding and Hemostasis in Laparoscopic Liver Surgery," Surg. Endos. 24(3)572-577.
(Continued)

*Primary Examiner* — Benjamin Packard
(74) *Attorney, Agent, or Firm* — William C. Schrot; AuerbachSchrot LLC

(57) ABSTRACT

Compositions comprising biomedical polymers, and in particular unique blends of poly(lactic-co-glycolic acid) (PLGA) and poly(ethylene glycol) (PEG) are provided. Methods of forming polymer fibers using such compositions and solution blow spinning techniques are also provided, as well as methods of delivering the blow spun polymer fibers onto a surface (e.g., such as tissue for use as a surgical scaffold, sealant or tissue adhesive).

28 Claims, 18 Drawing Sheets

Related U.S. Application Data filed on Jul. 18, 2014, provisional application No. 62/087,642, filed on Dec. 4, 2014.

(51) Int. Cl.
    *A61L 27/26*      (2006.01)
    *A61L 27/54*      (2006.01)

(56) References Cited

U.S. PATENT DOCUMENTS

| | | | |
|---|---|---|---|
| 8,181,643 | B2 | 5/2012 | Friedberg |
| 8,623,397 | B2 | 1/2014 | Ma et al. |
| 8,641,960 | B1 | 2/2014 | Medeiros et al. |
| 2003/0133980 | A1* | 7/2003 | Costantino ........... A61K 9/1647 424/468 |
| 2004/0236371 | A1 | 11/2004 | McNally-Heintzelman et al. |
| 2011/0189463 | A1 | 8/2011 | Moore et al. |
| 2011/0250257 | A1 | 10/2011 | Athur et al. |
| 2012/0240369 | A1 | 9/2012 | Capparelli Mattoso et al. |
| 2013/0164348 | A1 | 6/2013 | Palasis et al. |
| 2014/0079760 | A1 | 3/2014 | Schwartz et al. |

FOREIGN PATENT DOCUMENTS

| | | |
|---|---|---|
| WO | WO 2009/058990 | 5/2009 |
| WO | WO 2010/009335 | 1/2010 |
| WO | WO 2012/017415 | 2/2012 |
| WO | WO 2013/096709 | 6/2013 |
| WO | WO 2014/036290 | 3/2014 |

OTHER PUBLICATIONS

Agarwal, S. et al. (2008) "*Use of Electrospinning Technique for Biomedical Applications*," Polymer 49(26):5603-5621.

Albright, J.D. et al. (1967) "*Dimethyl Sulfoxide-Acid Anhydride Mixtures for Oxidation of Alcohols*," J. Am. Chem. Soc. 89(10):2416-2423.

Behrens, A.M. et al. (2014) "*In Situ Deposition of PLGA Nanofibers via Solution Blow Spinning*," ACS Macro Letters 3(3):249-254.

Bertram, J.P. et al. (2009) "*Intravenous Hemostat: Nanotechnology to Halt Bleeding*," Sci. Transl. Med. 1(11):11-22.

Brown, X.Q. et al. (2005) "*Evaluation of Polydimethylsiloxane Scaffolds with Physiologically-Relevant Elastic Moduli: Interplay of Substrate Mechanics and Surface Chemistry Effects on Vascular Smooth Muscle Cell Response*," Biomaterials 26(16):3123-3129.

Bruce, J. et al. (2001) "*Systematic Review of the Definition and Measurement of Anastomotic Leak After Gastrointestinal Surgery*," Br. J. Surg. 88(9):1157-1168.

Chang, E.I. et al. (2011) "*Vascular Anastomosis Using Controlled Phase Transitions in Poloxamer Gels*," Nat. Med. 17(9):1147-1153.

Chapman, W.C. et al. (2000) "*Effective Control of Hepatic Bleeding with a Novel Collagen-Based Composite Combined with Autologous Plasma: Results of a Randomized Controlled Trial*," Arch. Surg. 135(10):1200-1204.

Chittasupho, C. et al. (2009) "*ICAM-1 Targeting of Doxorubicin-Loaded PLGA Nanoparticles to Lung Epithelial Cells*," Eur. J. Pharm. Sci. 37(2):141-150.

Collet, J.P. et al. (2000) "*Influence of Fibrin Network Conformation and Fibrin Fiber Diamet on Fibrinolysis Speed*," Arterioscler Thromb. Vasc. Biol. 20(5):1354-1361.

Collet, J.P. et al. (2005) "*The Elasticity of an Individual Fibrin Fiber in a Clot*," Proc. Natl. Acad. Sci. U.S.A. 102(26):9133-9137.

Dalton, P.D. et al. (2006) "*Direct in Vitro Electrospinning with Polymer Melts*," Biomacromolecules 7(3):686-690.

Dowling, M.B. et al. (2011) "*A Self-Assembling Hydrophobically Modified Chitosan Capable of Reversible Hemostatic Action*," Biomaterials 32(13):3351-3357.

Furst, W. et al. (2005) "*Release of Glutaraldehyde from an Albumin-Glutaraldehyde Tissue Adhesive Causes Significant In Vitro and In Vivo Toxicity*," Ann. Thorac. Surg. 79(5):1522-1529.

Grethel, E.J. et al. (2006) "*Prosthetic Patches for Congenital Diaphragmatic Hernia Repair: Surgisis vs Gore-Tex*," J. Pediatric Surg. 41:29-33.

Harris, J.M. (1985) "*Laboratory Synthesis of Polyethylene-Glycol Derivatives*," J. Macromol. Sci. 25(3):325-373.

Hsiao, H.Y. et al. (2012) "*Effect of Air Blowing on the Morphology and Nanofiber Properties of Blowing-Assisted Electrospun Polycarbonates*," J. Appl. Polym. Sci. 124(6):4904-4914.

Hyman, N. et al. (2007) "*Anastomotic Leaks After Intestinal Anastomosis: It's Later Than You Think*," Ann. Surg. 245(2):254-258.

Jeong, Y.I. et al. (2011) "*Doxorubicin-Incorporated Polymeric Micelles Composed of Dextran-b-Poly(DL-Lactide-co-Glycolide) Copolymer*," Intl. J. Nanomed. 6:1415-1427.

Jing, Z. et al. (2003) "*Biodegradable Electrospun Fibers for Drug Delivery*," J. Control Release 92(3):227-231.

Kersten, S. et al. (2001) "*Fissure Sealing: Optimization of Sealant Penetration and Sealing Properties*," Am. J. Dentistry 14(3):127-131.

Khil, M.S. et al. (2003) "*Electrospun Nanofibrous Polyurethane Membrane as Wound Dressing*," J. Biomed. Mater. Res. B. Appl. Biomater. 67(2):675-679.

Kingham, T.P. et al. (2009) "*Colonic Anastomotic Leak: Risk Factors, Diagnosis, and Treatment*," J. Am. Coll. Surg. 208(2):269-278.

Langer, R. et al. (2004) "*Designing Materials for Biology and Medicine*," Nature 428(6982):487-492.

Lee, B.P. et al. (2011) "*Mussel-Inspired Adhesives and Coating*," Ann. Rev. Mater. Res. 41:99-132.

Li, H.B. et al. (2011) "*Photocrosslinkable Tissue Adhesive Based on Dextran*," Carbohyd. Polym. 86(4):1578-1585.

Li, W.J. et al. (2002) "*Electrospun Nanofibrous Structure: A Novel Scaffold for Tissue Engineering*," J. Biomed. Mater. Res. 60(4):613-621.

Lu, L. et al. (1999) "*In Vitro Degradation of Thin Poly(DL-Lactic-co-glycolic Acid) Films*," J. Biomed. Mat. Res. 46(2):236-244.

Mandavi, A. et al. (2008) "*A Biodegradable and Biocompatible Gecko-Inspired Tissue Adhesive*," PNAS 105(7):2307-2312.

Maia, J. et al. (2005) "*Synthesis and Characterization of New Injectable and Degradable Dextran-Based Hydrogels*," Polymer 46(23):9604-9614.

Makadia, H.K. et al. (2011) "*Poly Lactic-co-Glycolic Acid (PLGA) as Biodegradable Controlled Drug Delivery Carrier*," Polymers 3(3):1377-1397.

Medeiros, E.S. et al. (2009) "*Solution Blow Spinning: A New Method to Produce Micro- and Nanofibers from Polymer Solutions*," J. Appl. Polym. Sci. 113(4):2322-2330.

Moore, R.M. et al. (1940) "*Injections of Air and of Carbon Dioxide into a Pulmonary Vein*," Ann. Surg. 112(2):212-218.

Morten, A. et al. (2006) "*Animal Models in pediatric Surgery*," Pediatric Surg. Intl. 22(2):111-128.

Ng, W.S. et al. (1968) "*Carbon Dioxide in the Prevention of Air Embolism During Open-Heart Surgery*," Thorax 23(2):194-196.

Okamura, Y. et al. (2005) "*Hemostatic Effects of Fibrinogen Gamma-Chain Dodecapeptide-Conjugated Polymerized Albumin Particles In Vitro and In Vivo*," Transfusion 45(7):1221-1228.

Okamura, Y. et al. (2009) "*Novel Platelet Substitutes: Disk-Shaped Biodegradable Nanosheets and Their Enhanced Effects on Platelet Aggregation*," Bioconjug. Chem. 20(10):1958-1965.

Oliva, N. et al. (2015) "*Regulation of Dendrimer/Dextran Material Performance by Altered Tissue Microenvironment in Inflammation and Neoplasia*," Sci. Transl. Med. 7(272):1-8.

Oliveira, J.E. et al. (2011) "*Nano and Submicrometric Fibers of Poly(D,L-Lactide) Obtained by Solution Blow Spinning: Process and Solution Variables*," J. Appl. Polym. Sci. 122(5):3396-3405.

Oliveira, J.E. et al. (2012) "*Poly(Lactic Acid) / Carbon Nanotube Fibers as Novel Platforms for Glucose Biosensors*," Biosensors 2:70-82.

Oliveira, J.E. et al. (2013) "*Development of Poly(Lactic Acid) Nanostructured Membranes for the Controlled Delivery of Progesterone to Livestock Animals*," Mat. Sci. Eng. C. 33(2):844-849.

(56) References Cited

OTHER PUBLICATIONS

Oliveira, J.E. et al. (2013) "Structural and Morphological Characterization of Micro and Nanofibers Produced by Electrospinning and Solution Blow Spinning: A Comparative Study," Adv. Mater. Sci. Eng. 409572:14 Pages.

Pantelis, D. et al. (2010) "The Effect of Sealing with a Fixed Combination of Collagen Matrix-Bound Coagulation Factors on the Healing of Colonic Anastomoses in Experimental High-Risk Mice Models," Langenbecks Arch. Surg. 395(8):1039-1048.

Ritter, A.V. et al. (2009) "An Eight-Year Clinical Evaluation of Filled and Unfilled One-Bottle Dental Adhesives," J. Am. Dent. Assoc. 140:28-37.

Shoffstall, A.J. et al. (2012) "Intravenous Hemostatic Nanoparticles Increase Survival Following Blunt Trauma Injury," Biomacromol. 13(11):3850-3857.

Sinha-Ray, S. et al. (2010) "The Production of 100/400 nm Inner/Outer Diameter Carbon Tubes by Solution Blowing and Carbonization of Core-Shell Nanofibers," Carbon 48(12):3575-3578.

Sinha-Ray, S. et al. (2011) "Solution Blowing of Soy Protein Fibers," Biomacromolecules 12(6):2357-2363.

Slieker, J.C. et al. (2013) "Prevention of Leakage by Sealing Colon Anastomosis: Experimental Study in a Mouse Model," J. Surg. Res. 184(2):819-824.

Spotnitz, W.D. et al. (2008) "Hemostats, Sealants, and Adhesives: Components of the Surgical Toolbox," Transfusion 48(7):1502-1516.

Spotnitz, W.D. et al. (2012) "Hemostats, Sealants, and Adhesives III: A New Update as Well as Cost and Regulatory Considerations for Components of the Surgical Toolbox," Transfusion 52(10):2243-2255.

Srinivasan, S. et al. (2011) "Solution Spraying of Poly(Methyl Methacrylate) Blends to Fabricate Microtextured, Superoleophobic Surfaces," Polymer 52(14):3209-3218.

Tutak, W. et al. (2013) "The Support of Bone Marrow Stromal Cell Differentiation by Airbrushed Nanofiber Scaffolds," Biomaterials 34(10):2389-2398.

Von Burkersroda, F. et al. (2002) "Why Degradable Polymers Undergo Surface Erosion or Bulk Erosion," Biomaterials 23(21):4221-4231.

Wain, J.C. et al. (2001) "Trial of a Novel Synthetic Sealant in Preventing Air Leaks After Lung Resection," Ann. Thorac. Surg. 71(5):1623-1628.

Walk, R.M. et al. (2012) "T-Cell Activation is Enhanced by Targeting IL-10 Cytokine Production in Toll-Like Receptor-Stimulated Macrophages," ImmunoTargets and Therapy 1:13-23.

Wang, W.X. et al. (2009) "Biodegradable Thermoresponsive Microparticle Dispersions for Injectable Cell Delivery Prepared Using a Single-Step Process," Adv. Mater. 21(18):1809-1813.

Wang, Z.G. et al. (2009) "Enzyme Immobilization on Electrospun Polymer Nanofibers: An Overview," J. Mol. Catal. B: Enzymatic 56(4):189-195.

Yarin, A.L. et al. (2001) "Taylor Cone and Jetting from Liquid Droplets in Electrospinning of Nanofibers," J. Appl. Phys. 90(9):4836-4846.

Yuan, W. et al. (2011) "Surgical Wound Healing Using Hemostatic Gauze Scaffold Loaded with Nanoparticles Containing Sustained-Release Granulocyte Colony-Stimulating Factor," Intl. J. Nanomed. 6:3139-3149.

Zhu, Y. et al. (2013) "Aminolysis-Based Surface Modification of Polyesters for Biomedicals Applications," RSC Adv. 3(8):2509-2519.

Zhuang, X.P. et al. (2012) "Solution Blowing of Submicron-Scale Cellulose Fibers," Carbohydrate Polymers 90(2):982-987.

Zhuang, X.P. et al. (2013) "Solution Blown Nanofibrous Membrane for Microfiltration," J. Membrane Sci. 429:66-70.

Zosel, A (1985) "Adhesion and Tack of Polymers: Influence of Mechanical Properties and Surface Tensions," Colloid Polym. Sci. 263(7):541-553.

\* cited by examiner (A)

(B)

(C)

(A)

(C)

(D)

(B)

SOLUTION BLOW SPUN POLYMER FIBERS, POLYMER BLENDS THEREFOR AND METHODS AND USE THEREOF

CROSS-REFERENCE TO RELATED APPLICATIONS AND CLAIM TO PRIORITY

This application is based on U.S. Provisional Patent Application Ser. No. 61/979,054, filed Apr. 14, 2014, and U.S. Provisional Patent Application Ser. No. 62/026,073, filed Jul. 18, 2014, and U.S. Provisional Patent Application Ser. No. 62/087,642, filed Dec. 4, 2014, all entitled "Method and System for Solution Blow Spinning Polymer Nanofiber Sealants Utilizing Polymers, Modified Polymers, and Polymer Blends," which applications are incorporated herein by reference in their entireties and to which priority is claimed.

FIELD OF THE INVENTION

The present invention relates to compositions comprising biocompatible polymers, and in particular blends of PLGA and PEG, as well as methods of forming a blow spun polymer fiber construct, scaffold or sealant from such compositions on a surface in situ.

BACKGROUND OF THE INVENTION

Tissue reconstruction and closure of incisions or wounds is pertinent to almost all surgical interventions and traumatic injuries. Tissue sealants and hemostatic agents are sometimes utilized for preventing excess blood loss during surgical procedures. Current commercially available tissue sealants are composed of fibrin, glutaraldehyde, or synthetic hydrogel based materials. Fibrin sealants have relatively poor mechanical properties, and are relatively high in cost and complex to prepare for application. In addition, fibrin sealants pose a relatively high risk of disease transmission (Spotnitz W. D. & Burks S. (2012) "*Hemostats, sealants, and adhesives III: a new update as well as cost and regulatory considerations for components of the surgical toolbox*," Transfusion 52(10):2243-55). Glutaraldehyde-protein sealants are lower in cost as compared to fibrin sealants, but suffer from toxicity issues which severely restrict their clinical potential (Furst W. & Banerjee A (2005) "*Release of glutaraldehyde from an albumin-glutaraldehyde tissue adhesive causes significant in vitro and in vivo toxicity*," Annals of Thoracic Surgery 79(5):1522-9). Some conventional hydrogel sealants are non-cytotoxic and exhibit a lower risk of disease transmission as compared to fibrin sealants, but require complicated multi-step preparation and are prone to excessive swelling after use. Such swelling can cause injury to neighboring anatomic structures such as nerves or even the tissue involved (Spotnitz W. D. & Burks S. (2008) "*Hemostats, sealants, and adhesives: components of the surgical toolbox*," Transfusion 48(7): 1502-16). As a result of the problems and deficiencies associated with commerically available sealants, conventional suturing and tissue stapling remain ubiquitous to many procedures despite exhibiting limited capability, and few advances have been made with regard to improving these conventional techniques.

Polymer mats and scaffolds have been utilized for wound dressings (Khil M. S. et al. (2003) "*Electrospun nanofibrous polyurethane membrane as wound dressing*," J. Biomed. Mater. Res. B. 67B(2):675-9), and in various other biomedical applications including drug delivery (Jing Z. et al. (2003) "*Biodegradable electrospun fibers for drug delivery*," J. Control Release 92(3):227-231), tissue engineering (Li W. J. et al. (2002) "*Electrospun nanofibrous structure: A novel scaffold for tissue engineering*," J. Biomed. Mater. Res. 60(4):613-621), and enzyme immobilization (Wang Z. G. et al. (2009) "*Enzyme immobilization on electrospun polymer nanofibers: An overview*," J. Mol. Catal. B-Enzym. 56(4): 189-95). Nanofibers are typically generated by electrospinning, a process that utilizes an electric field applied to a drop of polymer melt or solution on the tip of a nozzle (Agarwal S. et al. (2008) "*Use of electrospinning technique for biomedical applications*," Polymer 49(26):5603-21). The droplet deforms forming a Taylor cone and a charged jet accelerates toward the target generating nanofibers (Yarin A. L. (2001) "*Taylor cone and jetting from liquid droplets in electrospinning of nanofibers*," J. Appl. Phys. 90(9):4836-46). Electrospinning requires specialized equipment, high voltages, electrically conductive targets, and suffers from a relatively low deposition rate. As such, the use of electrospinning for the direct deposition of fibers in surgical applications has not been permissible.

Accordingly, there is a need for an effective tissue sealant that is relatively inexpensive to fabricate, that may be readily deposited on any surface in situ, and that exhibits a relatively low risk of inflammatory response and disease transmission as compared to currently available sealants. There is also a need for improved methods of fabricating polymer fibers. The present invention is directed to compositions and methods that overcome some or all of the deficiencies associated with conventional sealant materials, devices and fabrication methods.

SUMMARY OF THE INVENTION

The present invention relates to compositions comprising biomedical polymers, and in particular unique blends of poly(lactic-co-glycolic acid) (PLGA) and poly(ethylene glycol) (PEG). The present invention also relates to methods of forming polymer fibers using such compositions and solution blow spinning techniques, as well as methods of delivering the blow spun polymer fibers onto a surface (e.g., such as tissue for use as a surgical scaffold, sealant or tissue adhesive).

As demonstrated herein, the adhesive strength of the polymer fibers may be modulated by an order of magnitude by depositing a thermally responsive blend of biomedical polymers utilizing solution blow spinning techniques. This ability to modulate adhesive strength, coupled with the ability to rapidly deposit the polymer fibers optimized for a particular site-specific application, has significant implications for many surgical procedures as well as for biomaterial fabrication.

Adhesive capabilities of the disclosed polymer sealants can be demonstrated utilizing various tests, e.g., shear (ASTM F2255), peel (ASTM F2256), tension (ASTM F2258), and wound closure strength (ASTM F2458) tests. Such tests are readily known to those of skill in the art. In addition, material shelf life can be assessed at multiple time points during testing. In vitro biocompatibility studies demonstrate cell viability. In vivo studies demonstrating biocompatibility include an intramuscular implant model and surgical efficacy in specific procedures using both small (mouse) and large (piglet) animal models. Biocompatibility of the disclosed sealant materials can also be assessed utilizing flow cytometry to quantify and qualify elevations in inflammatory cell infiltrate, which technique is adapted from tumor infiltrate evaluations in which tissue is lysed with intramuscular polymer implant, showing no significant increase in inflammatory cell response as compared to a control procedure without the disclosed sealant material. Furthermore, pre-clinical findings in tested models validate translation to clinical application of the disclosed sealant materials.

A biocompatible composition according to an embodiment of the present invention comprises a solution of between about 1% and about 20% weight per volume (w/v) poly(lactic-co-glycolic acid) PLGA, and a solution of between about 1% and about 20% w/v poly(ethylene glycol) (PEG). In some implementations, the composition comprise between about 3% and about 15% w/v PLGA. In some implementations, the composition comprises between about 1% and about 10% w/v PEG. In some implementations, the composition comprises about 10% w/v PLGA and about 5% w/v PEG. In some embodiments, the composition comprises a solution of PLGA having a weight average molecular weight of between about 50 kDa and about 200 kDa. In some implementations, the composition further comprises a solution of between about 1% and about 20% w/v PLGA having a weight average molecular weight of between about 1 kDa and about 20 kDa. In some implementations, the solution of PEG have a weight average molecular weight of between about 1 kDa and about 10 kDa. In some embodiments, the composition further comprises a volatile solvent, such as for example acetone or ethyl acetate. In some embodiments, one or both of the PLGA or PEG is modified to contain a therapeutic agent. The therapeutic agent may be, for example, a protein, a peptide, an amine, an aliphatic compound, and an antibiotic.

A biocompatible polymer fiber construct according to an embodiment of the present invention comprise blow spun polymer fibers formed from a composition comprising a solution of between about 1% and about 20% weight per volume (w/v) poly(lactic-co-glycolic acid) PLGA, and a solution of between about 1% and about 20% w/v poly (ethylene glycol) (PEG). In some implementations, the composition comprises a solution of between about 3% and about 15% w/v PLGA. The compositions may also or alternatively comprise a solution of between about 1% and about 10% w/v PEG. In some implementations, the composition comprises a solution of between about 10% w/v PLGA and about 5% w/v PEG. According to disclosed embodiments, the construct may be tissue sealant, adhesive material, hemostatic or scaffolding material. In some implementations, the polymer fibers forming the construct have an average diameter of less than about 500 nanometers (e.g., nanofibers or microfibers).

The present invention is also directed to a method of forming a polymer fiber construct, comprising the steps of: forming a plurality of polymer fibers using a solution blow spinning process, wherein the polymer fibers are formed from a composition comprising: i) a solution of between about 1% and about 20% weight per volume (w/v) poly (lactic-co-glycolic acid) PLGA; and ii) a solution of between about 1% and about 20% w/v poly(ethylene glycol) (PEG); and depositing the plurality of blow spun polymer fibers onto a target to form a conformal polymer fiber construct thereon. The composition may comprise between about 3% and about 15% w/v PLGA, and/or between about 1% and about 10% w/v PEG. In one implementation, the composition comprises about 10% w/v PLGA and about 5% w/v PEG. In some implementations, the target is a tissue surface. The polymer fiber construct may be formed on the tissue surface in vivo.

DETAILED DESCRIPTION OF EMBODIMENTS OF THE INVENTION

Figure 1:
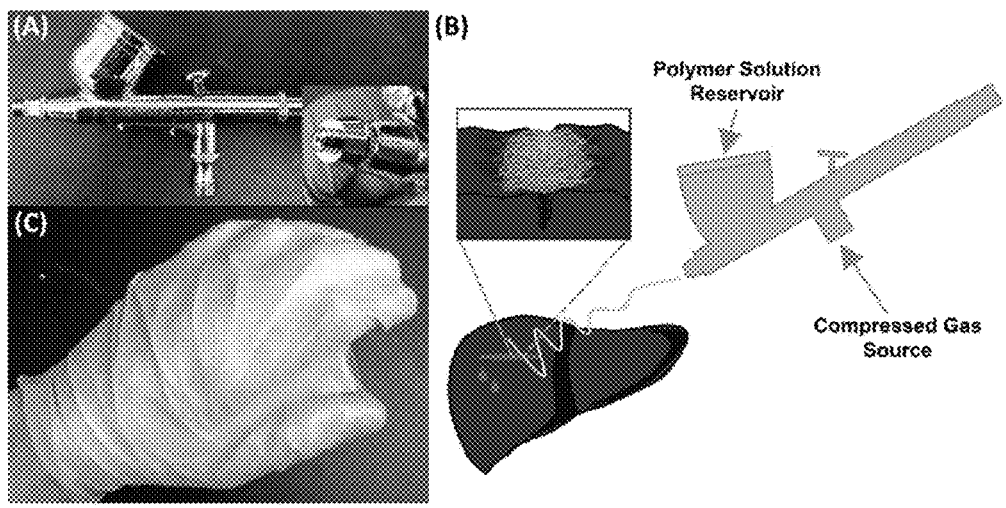
FIG. 1 includes an image of a commercial airbrush (Panel A) suitable for use as a blow spinning platform in accordance with disclosed embodiments. A schematic (Panel B) of an airbrush including a polymer solution reservoir and inlet for connecting a compressed gas source depicts polymer fiber deposition onto tissue. An image of conformal polymer fiber coating on a gloved hand is also shown (Panel C).

The present invention is directed to compositions comprising a biocompatible polymer(s) and a volatile solvent, and methods of forming and depositing blow spun polymer fibers formed from the disclosed compositions. In preferred embodiments, the composition comprises a blend of PLGA and PEG. The blow spun polymer fibers may be directly deposited onto any surface, including an irregular surface such as tissue, thereby generating a conformal polymer fiber construct such as a mat, mesh or scaffold. Such polymer fiber constructs may be readily formed in situ using solution blow spinning techniques.

Solution blow spinning requires a relatively simple apparatus, a concentrated polymer solution in a volatile solvent, and a compressed gas source (Medeiros E. S. et al. (2009) "*Solution Blow Spinning: A New Method to Produce Micro- and Nanofibers from Polymer Solutions*," J. Appl. Polym. Sci. 113(4):2322-30). Commercial airbrushes, typically used for painting, have successfully generated nanofibers through this technique (Srinivasan S. et al. (2011) "*Solution spraying of poly(methyl methacrylate) blends to fabricate microtextured, superoleophobic surfaces*," Polymer 52(14):3209-18; Tutak W. et al. (2013) "*The support of bone marrow stromal cell differentiation by airbrushed nanofiber scaffolds*," Biomaterials 34(10):2389-98). The ease of use and rapid deposition rates of solution blow spinning as compared to electrospinning have been reported (Medeiros E. S. et al. (2009) "*Solution Blow Spinning: A New Method to Produce Micro- and Nanofibers from Polymer Solutions*," J. Appl. Polym. Sci. 113(4):2322-30; Tutak W. et al. (2013) "*The support of bone marrow stromal cell differentiation by airbrushed nanofiber scaffolds*," Biomaterials 34(10):2389-98; Oliveira J. E. et al. (2011) "*Nano and Submicrometric Fibers of Poly(D,L-Lactide) Obtained by Solution Blow Spinning: Process and Solution Variables*," J. Appl. Polym. Sci. 122 (5): 3396-405).

Solution blow spinning may be utilized in applications including enzyme immobilization (Oliveira J. E. et al. (2012) "*Poly(lactic acid)/Carbon Nanotube Fibers as Novel Platforms for Glucose Biosensors*," Biosensors 2012(2):70-82), drug delivery (Oliveira J. E. et al. (2013) "*Development of poly(lactic acid) nanostructured membranes for the controlled delivery of progesterone to livestock animals*," Mat. Sci. Eng. C-Mater. 33(2):844-9), and microfiltration (Zhuang X. P. et al. (2013) "*Solution blown nanofibrous membrane for microfiltration*," J. Membrane Sci. 429:66-70). Further, solution blow spinning does not have the high voltage or conductivity requirements of electrospinning, and is an extremely portable and low cost alternative to electrospinning, allowing for the direct deposition of polymer fiber constructs that immediately set on any surface.

The disclosed compositions utilized in conjunction with direct deposition methods introduce a host of new applications and advantages over existing pre-formed mats, which traditionally require large stationary machinery and long fabrication times. On demand fabrication of conformal polymer fiber mats or scaffolds allows for precise and site specific construction within minutes, and thus finds particular utility as a surgical sealant for in vivo applications. The disclosed deposition methods require a relatively simple platform (e.g., a concentrated polymer solution, airbrush, and compressed gas source), and are thus versatile and adaptable to many applications. Thus, the disclosed polymer fiber sealants offer unique and distinct advantages over pre-formed polymer fiber mats and meshes, avoiding many pitfalls of conventional techniques and materials. Advantages include improvements in cost, speed, and safety, as compared to conventional polymer fiber fabrication techniques such as electrospinning.

The utilization of solution blow spinning in conjunction with the disclosed compositions is particularly useful in surgical procedures requiring the use of a hemostatic material or sealant, especially when large raw surfaces are exposed and conventional suturing may not be adequate or sufficient such as in the case with liver, lung and partial kidney resections (Chapman W. C. et al. (2000) "*Effective control of hepatic bleeding with a novel collagen-based composite combined with autologous plasma: results of a randomized controlled trial*," Arch Surg. 135(10):1200-1204; Abu Hilal M. et al. (2009) "*Bleeding and hemostasis in laparoscopic liver surgery*," Surg. Endosc. 24(3):572-577; Wain J. C. et al. (2001) "*Trial of a novel synthetic sealant in preventing air leaks after lung resection*," Annals of Thoracic Surgery 71(5):1623-1628). The blow spun polymer fiber mats or scaffolds formed in accordance with disclosed embodiments may either replace or augment conventional sutures, sealant materials, or hemostatic materials in a wide range of surgical applications, such as, but not limited to e.g., vascular, intestinal, or airway anastomosis, cerebrospinal fluid leak and other neurological or head and neck procedures, open wound and burn wound procedures, and other tissue reconstruction procedures. Such applications can be technically challenging, particularly when complications of leakage occur, which can result in high morbidity and even mortality (Chang E. I. et al. (2011) "*Vascular anastomosis using controlled phase transitions in poloxamer gels*," Nat Med. 17(9):1147-1160; Hyman N. et al. (2007) "*Anastomotic leaks after intestinal anastomosis: it's later than you think*," Annals of Surgery 245(2):254-8).

According to embodiments of the present invention, a system for solution blow spun polymer fiber sealants utilizes a concentrated polymer solution, a blow spinning platform, and a high pressure gas source (FIG. 1). Suitable blow spinning platforms may comprise an airbrush, an aerosol canister, or a laparoscopic device. The airbrush or other device is used in conjunction with the high pressure gas source as known in the art, which may comprise pressurized hydrogen, nitrogen, carbon dioxide, or another gas. In preferred embodiments, pressured $CO_2$ is utilized given its wide availability in modern operating rooms. In addition, other compressed gasses may carry the risk of air embolism; $CO_2$ avoids this complication due to its solubility in blood (Ng W. S. & Rosen M. (1968) "*Carbon dioxide in the prevention of air embolism during open-heart surgery*," Thorax 23:194-6; Moore R. M. & Braselton C. W. (1940) "*Injections of Air and of Carbon Dioxide into a Pulmonary Vein*," Ann. Surg. 112:212-8). The system is operable for forming polymer fibers onto a selected target surface, including nanofibers having diameters less than about 100 nanometers, as well as fibers having diameters orders of magnitude smaller than 100 nanometers (e.g., such as "microfibers") or larger than 100 nanometers, and additionally fibers or materials comprising a nanofiber/polymer composite.

The composition comprises a polymer solution, preferably PLGA or a similar biocompatible polymer such as poly(lactic acid) or polycaprolactone. In preferred embodiments, the composition comprises a blend of one or more polymers including PLGA, PEG, poly(lactic acid), polycaprolactone, dextran, and/or another biocompatible polymer or polysaccharide. In one implementation, the polymer solution comprises lactic acid and glycolic acid (e.g., 50:50). In preferred embodiments, the composition also comprises a volatile solvent, such as acetone or another similar chemical. The composition may be used at room temperature, heated, or cooled. The polymer solution may be formed at any concentration with any of the above-noted polymers or similar polymers or blends thereof, such as between about 1% and about 50% weight by volume (wt/vol), and with a range of polymer molecular weights or a combination of molecular weights.

Suitable polymers for use in the disclosed compositions may have a linear, branched, or star structure. Furthermore, suitable polymers may be chemically combined to create block-co-polymers or branched polymers. The polymers may also be chemically modified to contain reactive side or end groups, as discussed in further detail below. These reactive side or end groups may be contained within or added to any of the aforementioned polymers or similar polymers, and may include, e.g., aldehyde, epoxide, aliphatic chains, quinones, amines, peptides, sugars, amino acids, proteins, cyanoacrylates, N-hydroxysulfosuccinimide (NHS), thiols, or another similar molecule or chemical that will aid in general adhesion, tissue adhesion, or illicit a desired biological response.

Figure 2:
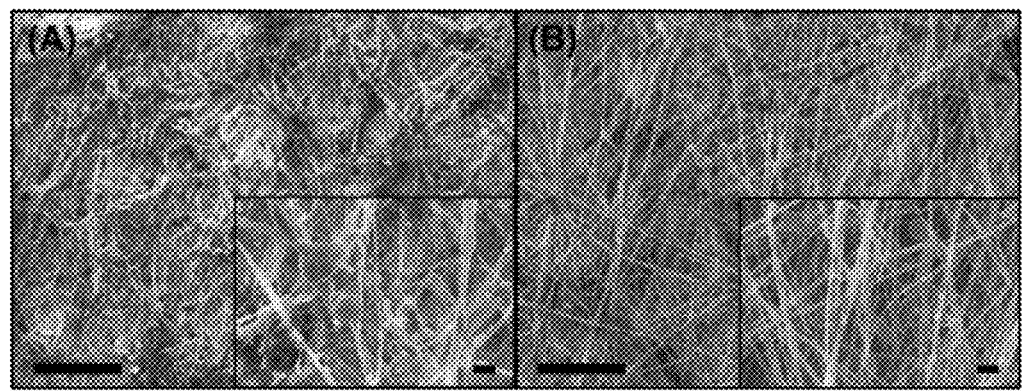
FIG. 2 are scanning electron micrograph (SEM) images of blow spun nanofibers formed from a solution of 10% PLGA (wt/vol) and 90% acetone (wt/vol). Variations in molecular weight and viscosity were determined to greatly affect fiber morphology. Panel A shows nanofibers formed from a solution of 0.64 IV (dL/g) PLGA at a $CO_2$ flow rate of 13 SCFH. Panel B shows nanofibers formed from a solution of 0.93 IV PLGA at a $CO_2$ flow rate of 13 SCFH. Larger scale bars in Panels A and B are 100 µm and smaller inset scale bars are 10 µm.

Polymer fiber constructs formed in accordance with disclosed embodiments are biodegradable and biocompatible. In addition, by adjusting the polymer solution properties (e.g. mass percentage, molecular weight, solvent, polymer, and/or viscosity) and/or the flow properties of the blow spinning platform (e.g. nozzle size, temperature, gas type and/or flow rate), the morphology of the resulting polymer fibers may be readily altered (FIG. 2). Alterations in fiber morphology affect mechanical and adhesive properties. For example, adhesive properties may be enhanced by blending a high molecular weight polymer (e.g., between about 50 kDa and about 200 kDa) with a lower molecular weight compound (e.g., PLGA and/or PEG). In one implementation, a solution comprising PLGA having molecular weights of 60 to 150 kDa at concentrations of 3%-10% (wt/vol) in acetone is blended with low molecular weight PLGA (5-15 kDa) in a similar concentration range. In addition to PLGA, the solution also preferably comprises low molecular weight PEG (1-10 kDa). This blend allows for tunable hydrophilicity and further control over adhesive strength, degradation rates, and mechanical properties. Further, PEG acts as a plasticizer for PLGA.

Functionalizations or modifications may also be utilized to achieve desired levels of tissue adhesion or biological response. Any synthetic chemical functionalization strategy presents challenges, such as the resulting polymer solubility. Such challenges may be overcome by using a different solvent mixture, such as ethyl acetate. In addition, device modifications, such as including a heating element in the tip of the apparatus, may be implemented if difficulties are encountered due to changes in the evaporation rate. While any polymer modification may potentially cause biocompatibility issues not seen in the non-functionalized polymer blend, such challenges do not pose an issue to the disclosed materials of the present invention. A catalog of bioadhesive functionalities on both PLGA and PEG may be synthesized and characterized for material strength, adhesive strength, and degradation. The preferred functionalized materials demonstrate adhesive properties that are enhanced and/or superior to non-functionalized material counterparts. In addition, the preferred functionalized materials do not negatively impact biocompatibility.

In some implementations, the polymers are modified to contain biologically interacting groups such as proteins, peptides, aliphatic groups, or antibiotics. The polymers may also be modified in order to enhance platelet targeting and/or cell adhesion moieties, such as with arginylglycylaspartic acid (RGD), H12 polypeptide, hydrophobic, von Willebrand's factor, or glycoprotein IIb/IIIa inhibitor interacting groups (e.g., see Bertram, J. P. et al. (2009) "*Intravenous Hemostat: Nanotechnology to Halt Bleeding*," Sci. Transl. Med. 1(11); Okamura, Y. et al. (2009) "*Novel Platelet Substitutes: Disk-Shaped Biodegradable Nanosheets and their Enhanced Effects on Platelet Aggregation*," Bioconjugate Chem. 20(10):1958-1965; Okamura, Y. et al. (2005) "*Hemostatic effects of fibrinogen gamma-chain dodecapeptide-conjugated polymerized albumin particles in vitro and in vivo*," Transfusion 45(7):1221-1228; Dowling, M. B. et al. (2011) "*A self-assembling hydrophobically modified chitosan capable of reversible hemostatic action*," Biomaterials 32(13):3351-3357).

Functionalization may be achieved through various means. For example, using PLGA-co-poly(lysine) coupled with 1-Ethyl-3-(3-dimethylaminopropyl)carbodiimide (EDC) allows for the attachment through the primary amine of the poly(lysine) block to any peptide or protein. Amines may also be introduced by utilizing aminolysis via the addition of 1,6-hexanediamine or amine addition through reaction with hydrazine. Glutaraldehyde may also be used to attach protein or peptide to the polymer.

Polymer fiber constructs formed from the disclosed compositions are particularly suitable for use as a surgical sealant or hemostatic material. Bleeding may be effectively and precisely controlled by blow spinning polymer fibers directly onto the target tissue (FIG. 1). The highest incidences of bleeding occur in cardiovascular surgery, liver transplantation, hepatic resections, and major orthopedic procedures. The blow spun fibers adhere to the targeted tissue and directly interact with platelets, red blood cells, and proteins. The sprayable hemostatic fibers are thus advantageous over conventional methods for stopping major blood loss in surgery, given they conform to irregular and/or delicate tissue surfaces. Moreover, the disclosed polymer fibers and methods of deposition are less expensive, reduce the risk of disease transmission, and improve usability and patient outcome as compared to conventional materials and techniques.

The polymer fibers are also suitable for use as a bioadhesive to obliterate tissue layers or to join (native and/or synthetic) tissue structures. The polymer fibers are also suitable for use in fixating or securing native tissue or synthetic material at desired locations, either with or without accompanying sutures. The polymer fibers are also suitable for use as a patch material, such as for closing or covering tissue defects or reinforcing weak or vulnerable tissues, either with or without accompanying sutures. The polymer fibers are also suitable for use as a filling material, such as for filling a tissue defect, lumen, or cavity to obliterate any space therein. The polymer fibers are suitable for both permanent and temporary use applications. Thus, the polymer fiber constructs, mats and scaffolds formed in accordance with the present invention demonstrate utility in a wide range of applications, and particularly surgical and medical applications (e.g., hemostatics, chest wall reconstruction, hernia repairs, sealants, etc.).

Having described features and embodiments of the present invention, the same will be further understood through reference to the following additional studies, examples and discussion, which are provided by way of further illustration and are not intended to be limiting of the present invention.

PLGA Fiber Fabrication

Solution blow spinning is used to fabricate conformal mats of PLGA fibers in situ using a commercial airbrush and compressed $CO_2$ (FIG. 1, Panel A). This technique allows for rapid conformal polymer fiber deposition onto any substrate (FIG. 1, Panels B and C).

Figure 3:
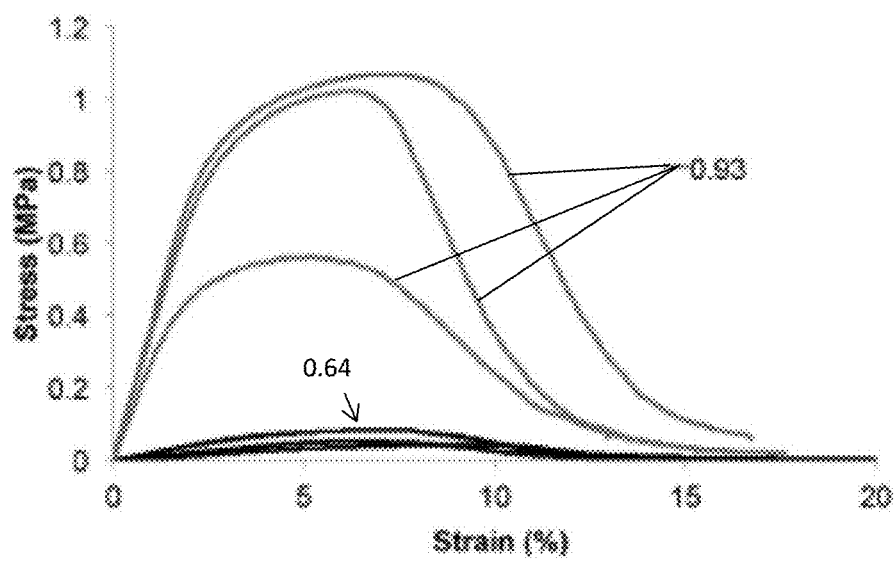
FIG. 3 illustrates graphically strain curves of 0.93 IV PLGA and 0.64 IV PLGA nanofiber mats (n=3) shown in FIG. 2.
Figure 20:
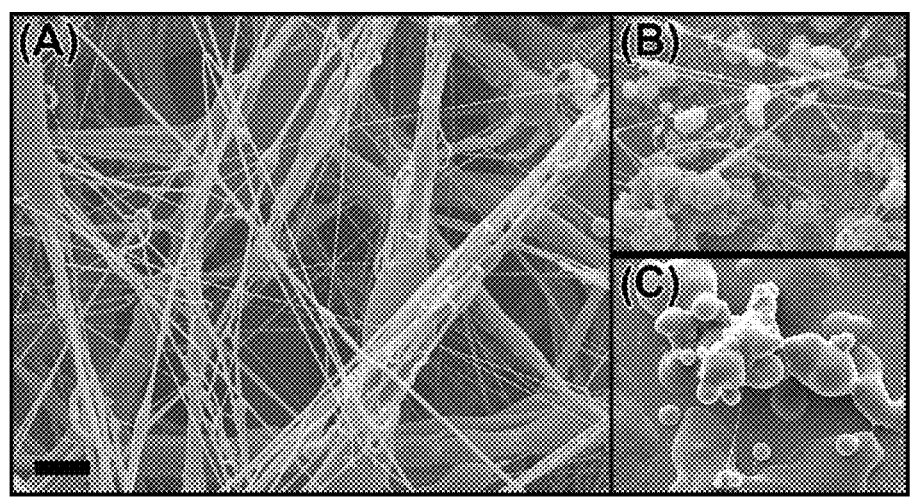
FIG. 20 are SEM images showing nanofiber morphology: Panel A shows 10% 15 kDa PLGA blended with 3% 100 kDa PLGA showing fiber morphology; Panel B shows 3% 100 kDa PLGA showing beads on a string morphology; Panel C shows 10% 15 kDa PLGA showing globular morphology. Scale bar represents 10 µm for all panels.

Solutions composed of 10% (wt/vol) PLGA of two different inherent viscosities, corresponding to higher and lower molecular weights, were investigated (0.93 dL/g and 0.64 dL/g PLGA) in acetone at three different gas flow rates (FIGS. 2 and 3). Considerations for polymer fiber generation include solution concentration, polymer molecular weight, solvent, and specific deposition conditions. An important parameter effecting the resulting morphology of solution blow spun fibers is the concentration (c) with respect to polymer chain entanglement, and specifically the overlap concentration (c*). Solutions with c>c* form fibers, solutions with c~c* form beads on a string morphology, and solutions with c<c* form a corpuscular morphology (FIGS. 2 and 20). Exemplary solution and deposition conditions resulting in rapid generation of uniform polymer fibers is 10% (w/v) 0.93 IV PLGA in acetone with a 13 SCFH $CO_2$ gas flow rate (FIG. 2, Panel B).

Figure 4:
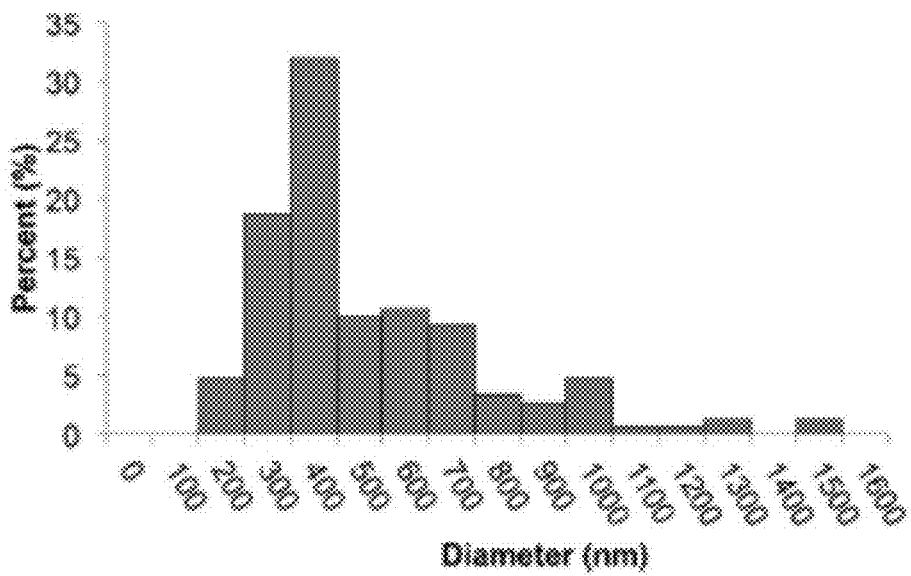
FIG. 4 illustrates graphically size distribution of nanofiber diameter for optimal solution and deposition conditions (n=150) of the nanofiber mats shown in FIG. 2.

Resulting polymer fiber mats had an average fiber diameter of 474±262 nm and a median value of 377 nm (FIG. 4). This range of fiber diameter is consistent with fibrin fiber diameter (~376 nm) (Collet, J. P. et al. (2000) "*Influence of fibrin network conformation and fibrin fiber diameter on fibrinolysis speed: dynamic and structural approaches by confocal microscopy*," Arterioscler. Thromb. Vasc. Biol. 20(5):1354-61). Dynamic mechanical analysis was performed to evaluate differences in mechanical properties between solution blow spun 0.93 IV and 0.64 IV PLGA (FIG. 3). The ultimate strength was determined by the maximum of the stress-strain curve and the Young's modulus by the slope between 0 and 1% strain. The 0.93 IV PLGA had an average ultimate strength of 0.88±0.28 MPa and a Young's modulus of 0.33±0.06 MPa. The 0.64 IV PLGA had an average ultimate strength of 0.06±0.02 MPa and a Young's modulus of 0.01±0.01 MPa. The mechanical properties of the 0.93 IV PLGA fiber mats were significantly better than the same deposition conditions using the 0.64 IV PLGA. The Young's modulus of the optimal mat (0.88 MPa) was comparable to that of fibrin (1-10 MPa) and many human tissues (~1 MPa) (Collet, J. P. et al. (2005) "*The elasticity of an individual fibrin fiber in a clot*," Proc. Natl. Acad. Sci. U.S.A. 102(26):9133-7; Brown, X. Q. et al. (2005) "*Evaluation of polydimethylsiloxane scaffolds with physiologically-relevant elastic moduli: interplay of substrate mechanics and surface chemistry effects on vascular smooth muscle cell response*," Biomaterials 26(16):3123-9). These characteristics are therefore well suited for in vivo use as tissue mimics in a variety of applications without the complications and costs associated with biologically derived materials.

Figure 5:
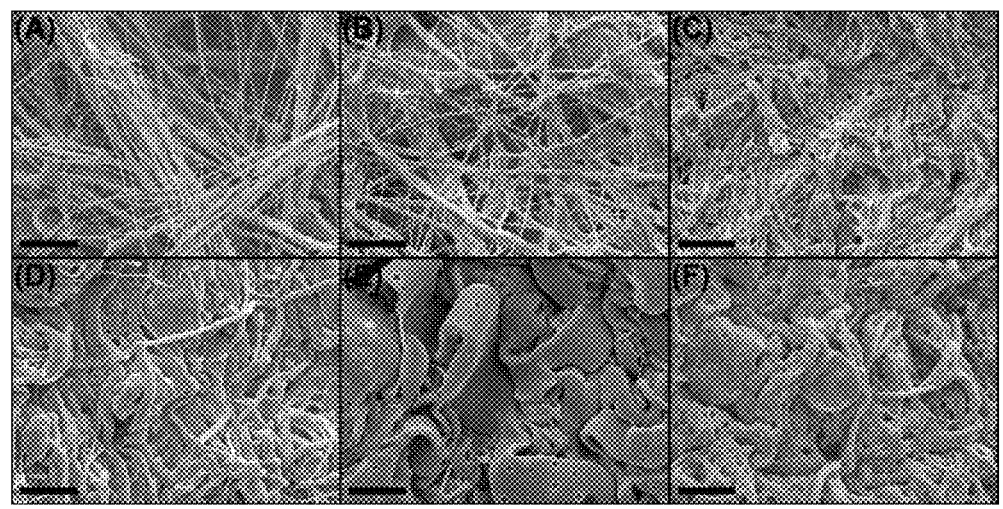
FIG. 5 are SEM images of PLGA nanofibers showing degradation of the nanofibers at 0 days (Panel A), 1 day (Panel B), 7 days (Panel C), 14 days (Panel D), thirty days (Panel E), and 42 days (Panel F). Scale bars correspond to 20 µm.
Figure 6:
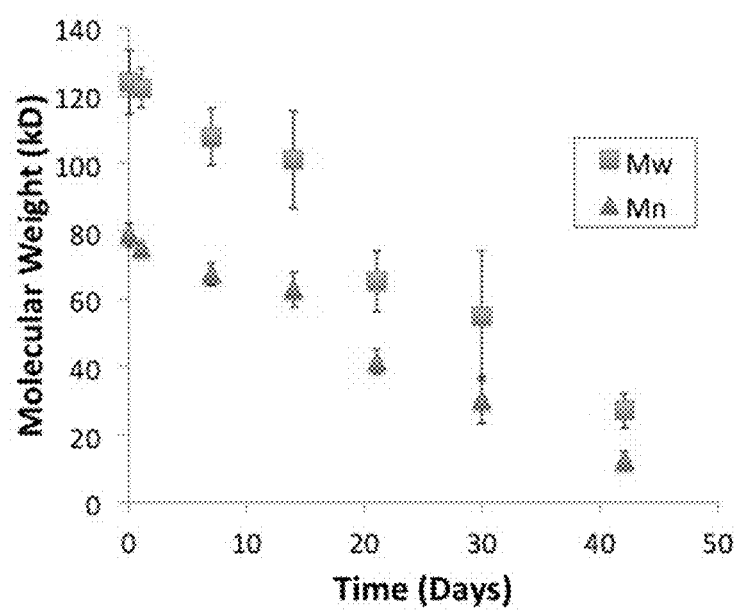
FIG. 6 illustrates graphically gel permeation chromatography (GPC) data of PLGA molecular weight change over 42 days, and corresponding to nanofiber degradation shown in FIG. 5 (n=3).
Figure 7:
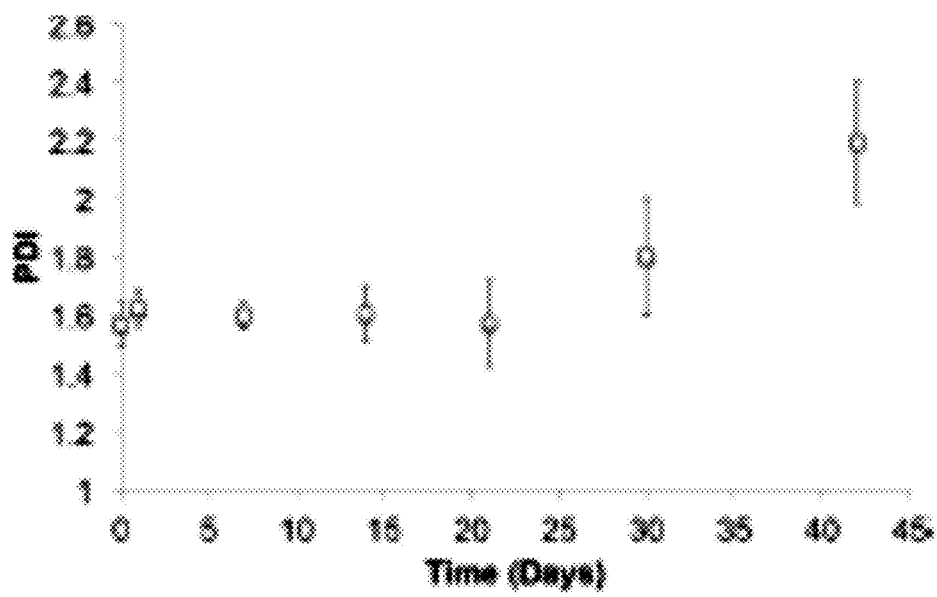
FIG. 7 illustrates graphically polydispersity index (PDI) change over the 42 day period of degradation of nanofibers shown in FIG. 5 (n=3).

After identifying optimal solution and deposition conditions, PLGA polymer fiber degradation was evaluated over 42 days for morphologic and molecular weight changes (FIGS. 5, 6 and 7). Polymer fiber morphology changed noticeably over this time scale. As fibers degraded, there was an increase in average diameter as a result of fibers fusing together, and a majority of the mat porosity was lost by day 7 (FIG. 5, Panel B). As degradation continued (7-42 days), fibers welded into each other forming a more homogeneous structure with evidence of obvious surface pitting and pore formation on day 30 and 42 (FIG. 5, Panel D). During this same time frame, weight average molecular weight (Mw) and number average molecular weight (Mn) decreased in a linear manner from day 0 at Mw=123.9±9.4 kDa and Mn=78.9±3.4 kDa to day 42 at Mw=27.2±5.1 kDa and Mn=12.5±2.6 kDa (FIG. 6). The polydispersity index (PDI) increased from 1.6±0.1 to 2.2±0.2 during this period (FIG. 7). This linear decrease in molecular weight over a 42 day period corresponds to a Mw decrease of ~78% and a Mn decrease of ~84%. A linear degradation profile is consistent with surface erosion in contrast to bulk erosion (von Burkersroda, F. et al. (2002) "*Why degradable polymers undergo surface erosion or bulk erosion*," Biomaterials 23(21):4221-31). The high surface area/volume of the fibers presumably allows for quicker diffusion and neutralization of the acidic degradation species that typically cause autocatalytic degradation in bulk erosion. This degradation profile may be altered by adjusting the ratio of lactic to glycolic acid in the copolymer (Lu, L. et al. (1999) "*In vitro degradation of thin poly(DL-lactic-co-glycolic acid) films*," J. Biomed. Mater. Res. 46(2):236-44).

PLGA/PEG Polymer Blends

The characterization, adhesive and sealant optimization and functionalization, and biocompatibility of polymer blends were assessed. Blends of PLGA and PEG were utilized as the platform material for biomedical sealant applications based on their biocompatibility, biodegradability, and low cost. The ability to directly apply conformal coatings of PLGA/PEG blends onto biologic and non-biologic substrates using a commercial airbrush and pressurized gas (e.g., $CO_2$) is demonstrated.

Blow spun polymer fiber mats are deposited from solutions with varying molecular weights of PLGA and PEG, varying PLGA/PEG blend ratios, and varying concentrations. Both polymer type and molecular weight impact fiber morphology and adhesive strength. Topical morphology is characterized by SEM. Differential scanning calorimetry (DSC) was used to evaluate phase separation and thermal behavior of the polymer fiber mats. Transmission electron microscopy (TEM) can also be used for evaluating phase separation and thermal behavior of the polymer mats. Mechanical properties are assessed by Dynamic Mechanical Analysis (DMA). Contact angle measurements and water absorption studies can be used to correlate material chemistries and morphologies to hydrophobicity/hydrophilicity. Degradation is monitored by mass loss, morphology change (SEM), and molecular weight change (gel permeation chromatography, (GPC)). Adhesive strength testing and cell viability assays assess material characteristics and biocompatibility. Such characteristics can also be assessed with inflammatory response and hemocompatibility assays.

In some embodiments, solutions were composed of 10% (w/v) PLGA and 5% (w/v) PEG (0.86 IV PLGA, 1 kDa PEG). Morphology and adhesive strength of the resulting PLGA/PEG fibers was compared to fibers formed from a solution of 10% PLGA without PEG (0.86 IV PLGA).

Figure 11:
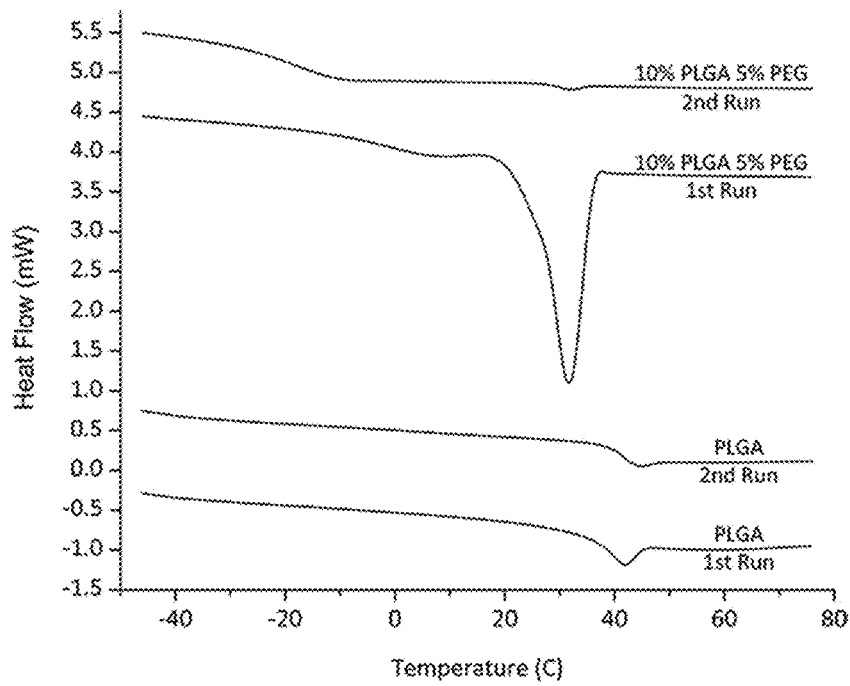
FIG. 11 illustrates graphically differential scanning calorimetry of PLGA/PEG polymer nanofiber mat blends demonstrating melting of PEG in a first heating cycle and plasticization of PLGA in a second heating cycle (Panel A). Plasticization is observed in the 10% PLGA/5% PEG (wt/vol) nanofiber mat upon heating to 37° C. (Panel B), while no plasticization is observed in 10% PLGA/0% PEG (wt/vol) nanofiber mat upon similar heating (Panel C).
Figure 11:
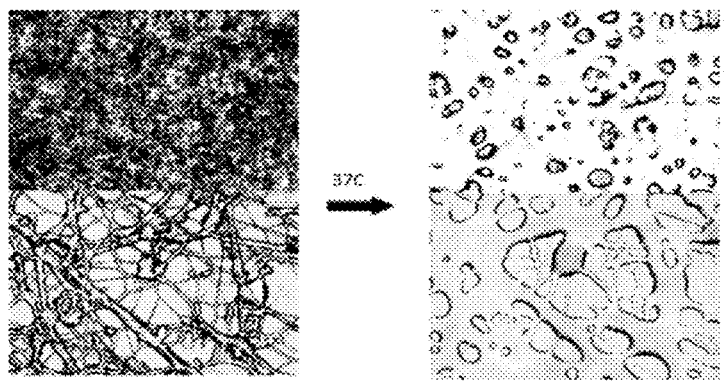
Figure 11:
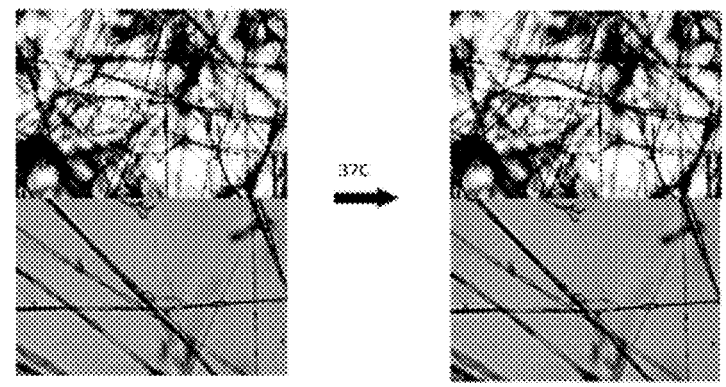
Figure 12:
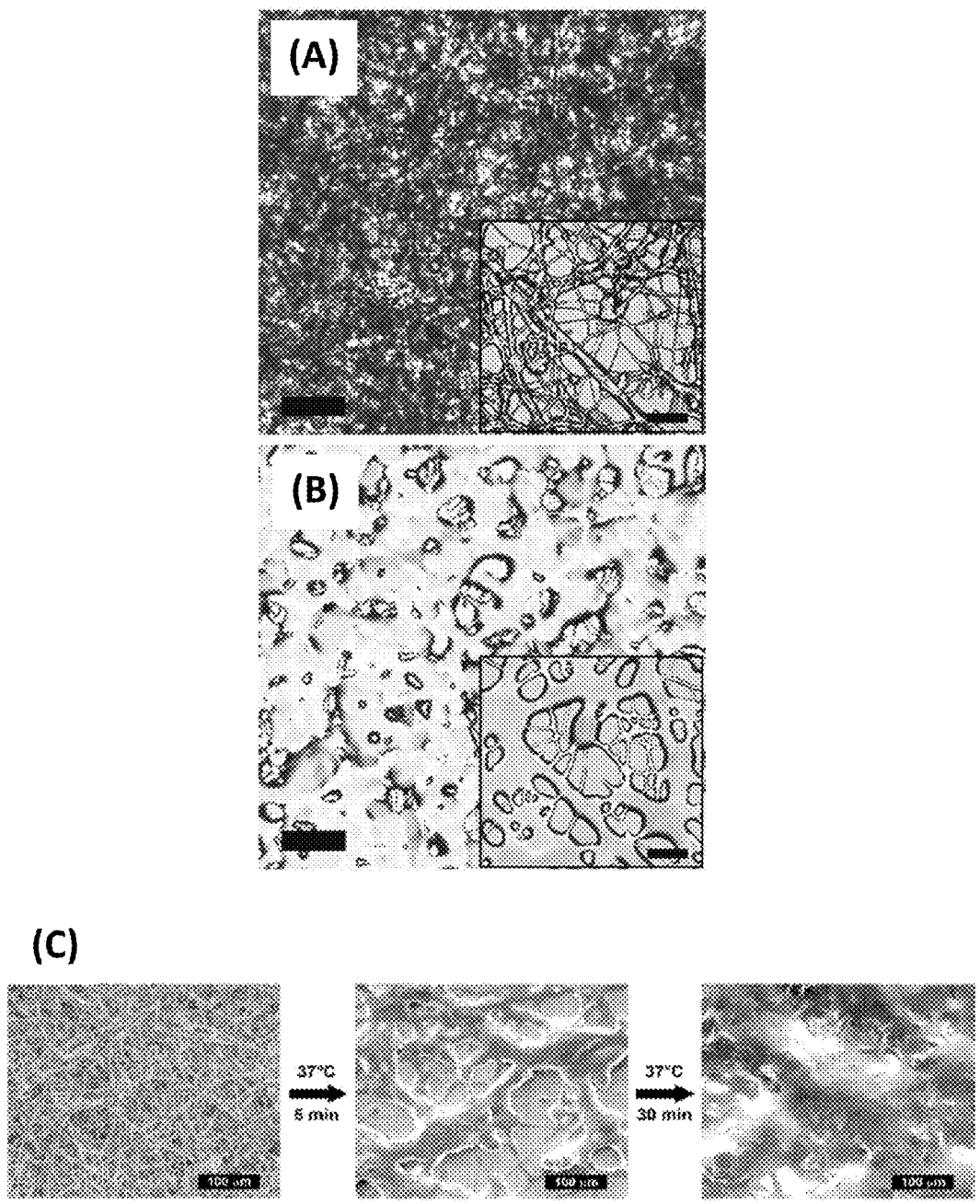
FIG. 12 are SEM images showing the 10% PLGA/5% PEG (wt/vol) blend welding together upon reaching the melting temperature of PEG and glass transition of PLGA, creating an adhesion-promoting interface with the underlying substrate. Blow spun fibers at room temperature (Panel A) form a film upon heating to 37° C. (Panel B). Morphology changes after 5 minutes and 30 minutes are shown in Panel C. Scale bars in Panels A, B and C represent 100 µm, and 25 µm in the inset in Panels A and B.

The ability to modulate adhesion through the use of PLGA/PEG blends that exhibit body temperature responsive adhesive behavior is demonstrated. After deposition of PLGA/PEG fibers onto a warm substrate (e.g., tissue at approximately 37° C.), the PEG component melts while the PLGA component of the blend softens above its glass transition, resulting in a plasticized polymer blend, as shown by differential scanning calorimetry (DSC) (FIG. 11). Upon these transitions, the polymer fibers weld together creating an adhesion-promoting interface with the underlying substrate (FIG. 12, Panels A and B). The material transitions occur in less than about 30 minutes (FIG. 12, Panel C).

Figure 13:
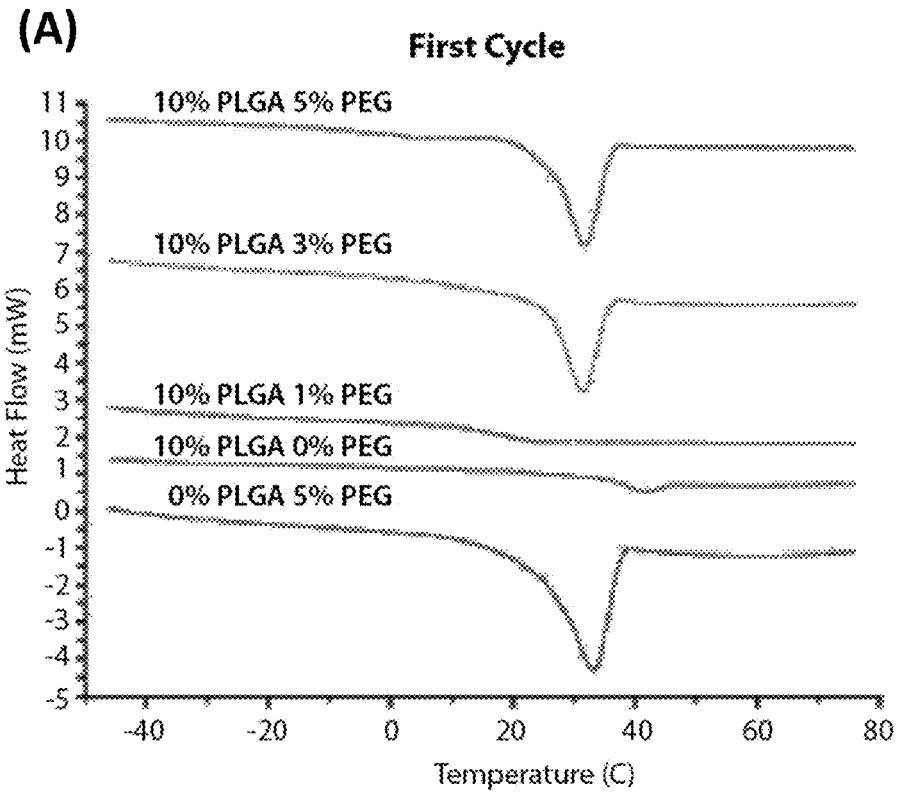
FIG. 13 illustrates graphically differential scanning calorimetry data of PLGA/PEG blends showing the melting of PEG in a first heating cycle (Panel A) and the plasticization of PLGA in a second heating cycle (Panel B).
Figure 13:
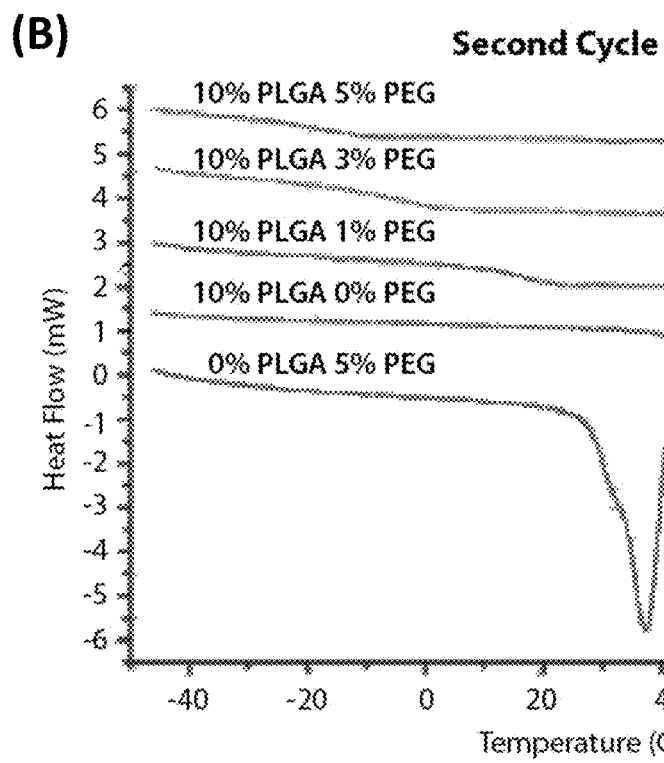

Observed PEG melting temperatures and PLGA glass transition temperatures (Tg) for various PLGA/PEG blends are shown in FIG. 13 and provided in the table below:

|  | Melting (C.) | | Tg (C.) | |
|  | 1st Cycle | 2nd Cycle | Heating | Cooling |
| --- | --- | --- | --- | --- |
| 10% PLGA 5% PEG | 31.61 | N/A | 10% PLGA 5% PEG | −18.03 | −19.96 |
| 10% PLGA 3% PEG | 31.40 | N/A | 10% PLGA 3% PEG | −3.6 | −6.42 |

-continued

| | Melting (C.) | | Tg (C.) | |
|---|---|---|---|---|
| | 1st Cycle | 2nd Cycle | Heating | Cooling |
| 10% PLGA 1% PEG | N/A | N/A | 10% PLGA 1% PEG 18.29 | 17.45 |
| 10% PLGA 0% PEG | N/A | N/A | 10% PLGA 0% PEG 42.07 | 39.15 |
| 0% PLGA 5% PEG | 33.19 | 30.98 | 0% PLGA 5% PEG N/A | N/A |

Figure 14:
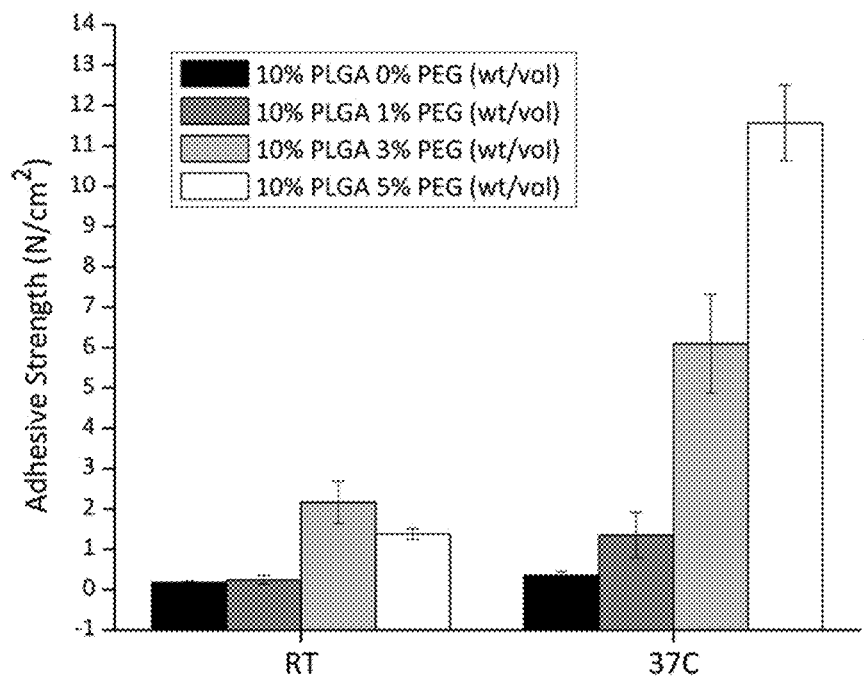
FIG. 14 illustrates graphically data from a tensile adhesion strength test using a mechanical tester (Instron Engineering Corp., MA) with temperature control, showing adhesion strength dependence on polymer blend content. 10% PLGA/5% PEG (wt/vol) polymer fibers show a body temperature dependent adhesive strength with approximately a 10-fold increase over PLGA alone.

This results in a significant increase in adhesive strength as compared to PLGA alone (FIG. 14). Thus, modulating molecular weight and using polymer blends offers the ability to further alter adhesive strength and control mechanical properties (Zosel A. (1985) "Adhesion and Tack of Polymers—Influence of Mechanical-Properties and Surface Tensions," Colloid and Polymer Science 263:541-53). Deposition and solution characteristics are thus readily optimized for a particular application.

Polymer Fiber mats were deposited from solutions containing 10% (wt/vol) PLGA and 0%-5% (wt/vol) PEG dissolved in acetone. These polymers are commonly investigated for a wide variety of biomedical applications such as drug delivery and tissue engineering. This broad usage can be attributed to their biocompatibility and bioabsorbability. Higher PEG content led to increased fiber diameter.

When deposited onto a warm substrate, the polymer fiber mats with higher PEG content (10% PLGA/3% PEG and 10% PLGA/5% PEG) undergo a melting transition between 31° C. and 32° C. This is in agreement with the melting temperature of the crystalline domains of PEG alone. Conveniently, melting occurs at a temperature that is bellow both topical and internal body temperatures. Upon reaching the crystal melting temperature, the fibers weld together and PLGA and PEG become miscible, creating a homogenous, transparent polymer film (FIG. 12). During film formation, the polymer blend orients to the warm substrate and becomes plasticized with a glass transition temperature ($T_g$) well below body temperature ($T_g$=-18° C. for 10% PLGA/5% PEG), resulting in increased polymer-substrate interaction. After the initial melting event the recrystallization of PEG is suppressed in all cases except for the pure PEG sample (FIG. 13). Correspondingly, adhesive strength drastically increases for the high PEG content blends after incubation at 37° C. 10% PLGA/3% PEG and 10% PLGA/5% PEG blends reached much higher adhesive strengths than PLGA alone at either room temperature or 37° C. and to the same blends at room temperature.

Cell Viability

Figure 15:
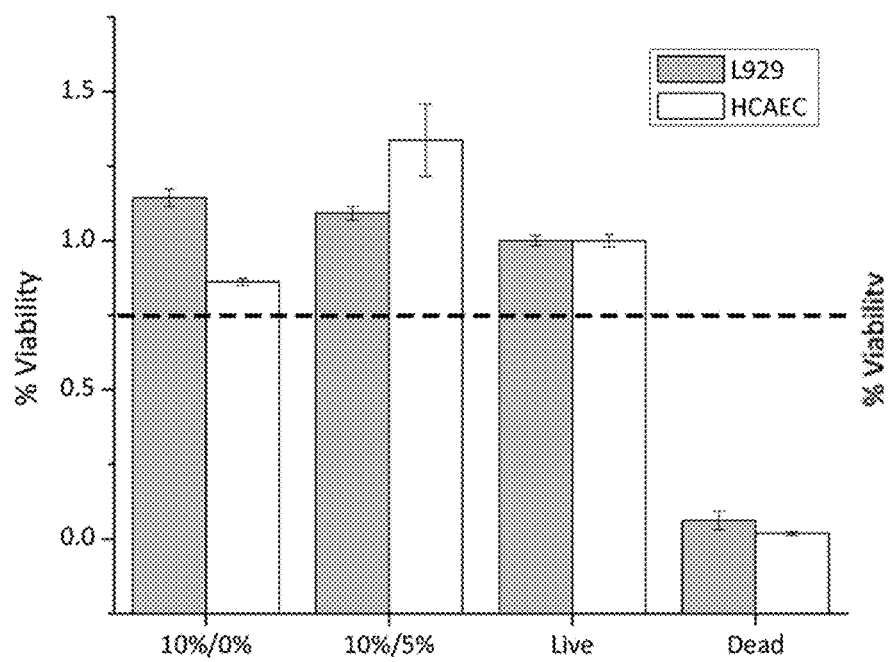
FIG. 15 illustrates graphically cell viability of L929 mouse fibroblasts and human coronary artery endothelial cells (HCAEC) seeded on top of PLGA and PLGA/PEG for 24 hours. Cell viability was not detrimentally impacted. Viability is reported as percent of the live control, tissue culture polystyrene, using an MTS cell viability assay. The dotted line indicates 75% viability.
Figure 16:
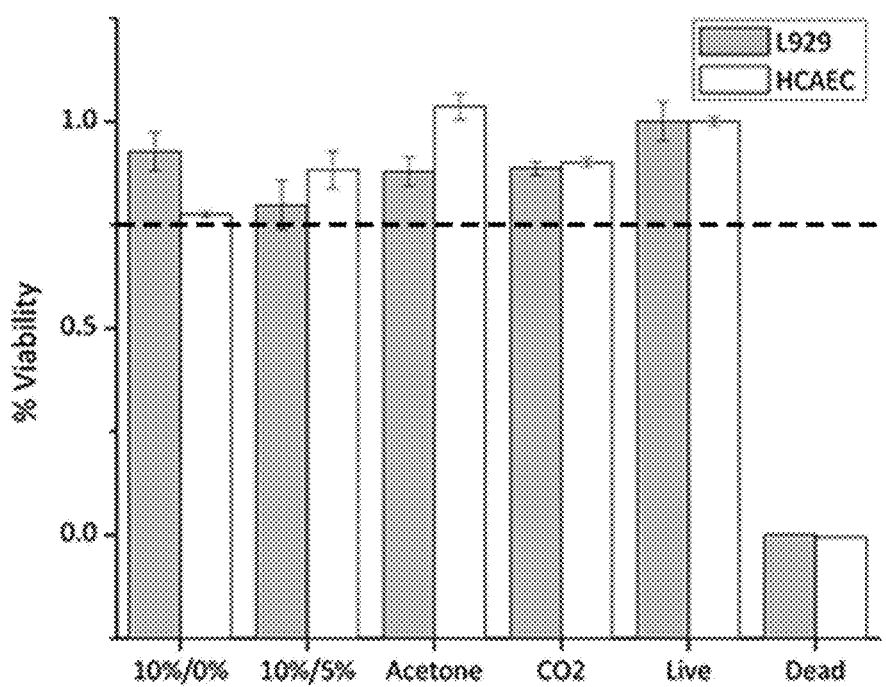
FIG. 16 illustrates graphically cell viability of L929s and HCAECs after direct deposition of PLGA and PLGA/PEG polymer fibers using solution blow spinning. Cell viability was not detrimentally impacted. Viability is reported as percent of the live control, tissue culture polystyrene, using an MTS cell viability assay. The dotted line indicates 75% viability.

In vitro cell viability studies to evaluate toxicity of PLGA and PLGA/PEG blends were performed using L929 mouse fibroblasts and human coronary arterial endothelial cells (HCAEC). Viability is reported as percent of the live control, tissue culture polystyrene, using an MTS cell viability assay. Viability was evaluated after the cells were seeded on top of PLGA and PLGA/PEG for 24 hours (FIG. 15). Cells were cultured to 75% confluency then sprayed with polymer fibers. After 24 hours, MTS reagent was added to the culture, where reagent in the supernatant changes colors in response to cellular metabolic activity. A 30-minute exposure with 70% methanol solution was used as the dead control. Cell viability of L929s and HCAECs was also evaluated after direct deposition of blow spun PLGA and PLGA/PEG polymer fibers (FIG. 16). In both studies, cell viability was not detrimentally impacted. Similarly, metabolic activity was not detrimentally impacted for either cell line sprayed with PLGA/PEG polymer fibers (FIGS. 15 and 16).

Figure 17:
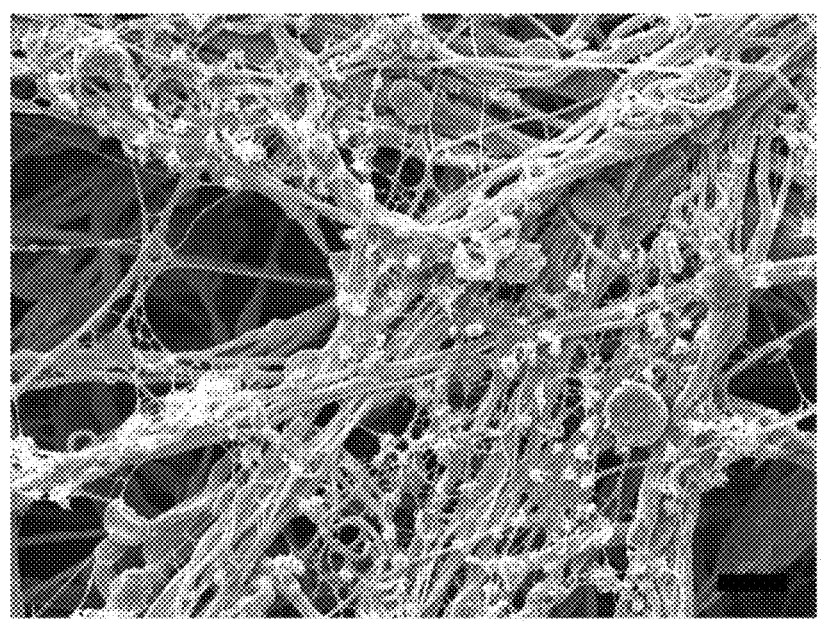
FIG. 17 is a SEM image of PLGA nanofibers incubated with citrated whole human blood. Scale bar represents 10 µm.

Qualitative evaluation of blood interaction with nanofiber mats was completed using SEM (FIG. 17). After an hour incubation and washing with PBS there was significant platelet and erythrocyte adsorption onto the nanofiber matrix. The best material candidates were selected for further in vitro mechanical testing and toxicity assays for assessing tissue adhesion and biocompatibility, and for demonstrating in vivo efficacy.

Blow Spun PLGA/PEG Blend Optimization

Optimal molecular weight ranges for attaining fiber morphology via solution blow spinning are determined Relatively high molecular weight polymers (e.g., greater than about 50 kDa, or between about 50 kDa and about 200 kDa) are blended with lower molecular weight PLGA and PEG to alter mechanical properties and improve adhesive properties. Fiber forming PLGA molecular weights of about 50 to about 200 kDa, or about 60 to 150 kDa, at concentrations of 3%-10% (w/v) in ethyl acetate or acetone are blended with low molecular weight PLGA (e.g., 5-15 kDa) in similar concentration ranges. Blending high and low molecular weight polymer allows for modulation of adhesive and mechanical properties.

Blending with low molecular weight PEG (e.g., 1-10 kDa) allows for tunable hydrophilicity and further control over adhesive strength, degradation rates, and mechanical properties. Furthermore, PEG acts as a plasticizer for PLGA, thereby lowering the glass transition temperature ($T_g$) of PLGA and allowing for an improved polymer/tissue interface at physiological temperature (Wang W. X. et al. (2009) "Biodegradable Thermoresponsive Microparticle Dispersions for Injectable Cell Delivery Prepared Using a Single-Step Process," Advanced Materials 21:1809). In some studies, 50:50 lactic acid to glycolic acid is used with a commercial airbrush and compressed $CO_2$. This ratio may be modulated later to achieve different material strengths and degradation rates as required by each specific application (Lu L. et al. (1999) "In vitro degradation of thin poly(DL-lactic-co-glycolic acid) films," J. Biomed. Mat. Res. 46(2):236-44). The 50:50 ratio of lactic acid to glycolic acid was selected to match the degradation profile of the sutures used with the solution blow spun sealant in the intestinal anastomosis model studies, as described in further detail below.

Figure 18:
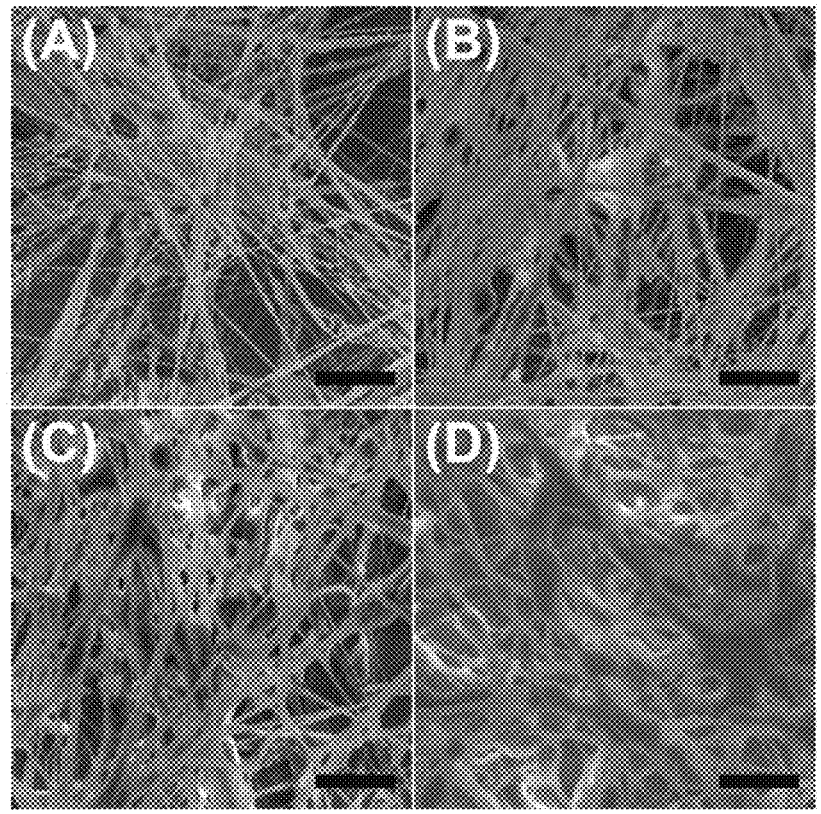
FIG. 18 is a SEM image of solution blow spun PLGA/PEG blends showing changes in fiber mat morphology with increasing PEG content: 10% PLGA and 0% PEG (wt/vol) is shown in Panel A; 10% PLGA and 1% PEG (wt/vol) is shown in Panel B; 10% PLGA and 3% PEG (wt/vol) is shown in Panel C; 10% PLGA and 5% PEG (wt/vol) is shown in Panel D. Scale bars represent 20 µm.

For each polymer blend, the polymer mat morphology was characterized by SEM. Significant effects on fiber morphology were demonstrated with blending (FIG. 18). In addition, transmission electron microscopy (TEM) can be coupled with staining techniques to image the phase separation behavior in the polymer blend fiber constructs. Differential scanning calorimetry (DSC) and dynamic mechanical analysis (DMA) is also utilized to investigate plasticization, phase transitions, and mechanical properties of the polymer blends. Material strength comparable to that of many human tissues (~1 MPa) is thereby achieved (see Brown X. Q. et al. (2005) "Evaluation of polydimethylsiloxane scaffolds with physiologically-relevant elastic moduli: interplay of substrate mechanics and surface chemistry effects on vascular smooth muscle cell response," Biomaterials 26:3123-9). Hydrophilicity, which has implications in degradation and adhesion, is assessed through contact angle measurements. Additionally, water absorption values can be assessed at time intervals between 1 and 24 hours at 37° C., in accordance to ASTM D570.

Adhesive Strength

A modified pull-off test was used to assess differences in adhesion strength among the different PLGA/PEG polymer blends. Results indicated tensile adhesion strength dependence on polymer blend content (FIG. 14). For example, 10% PLGA/5% PEG polymer blend showed a body temperature dependent adhesive strength with a more than 10-fold increase as compared to PLGA alone.

Adhesive strength can also be assessed using shear (ASTM F2255), peel (ASTM F2256), tension (ASTM F2258), and wound closure strength (ASTM F2458) tests. For example, the polymer fibers may be sprayed directly at the union of two separate pieces of the tissue of interest, or applied to a single side in the case of the peel test, and therefore assessed (e.g., using a mechanical tester) by applying strain with both samples in plane or in the appropriate orientation according to the ASTM.

In Vitro Degradation

Material candidates with the best balance of mechanical strength and adhesive strength were selected for further in vitro degradation studies. Polymer fiber mats were fabricated and submerged in appropriate media at physiological conditions (1× phosphate buffered saline (PBS) and simulated body fluid at 37° C.) on a shaker incubator, and aged according to ASTM F1635. Degradation was monitored until complete polymer dissolution, which as expected occurs at 6-8 weeks consistent with previous PLGA degradation studies (FIGS. 5, 6 and 7). At predetermined time points, mechanical properties were assessed with DMA. SEM is used to visualize morphologic changes. Gel permeation chromatography (GPC) is used to monitor molecular weight changes. Polymer weight fractions of the polymer blends is also monitored by GPC over time, as lower molecular weight PLGA and PEG are expected to degrade or solubilize.

Figure 8:
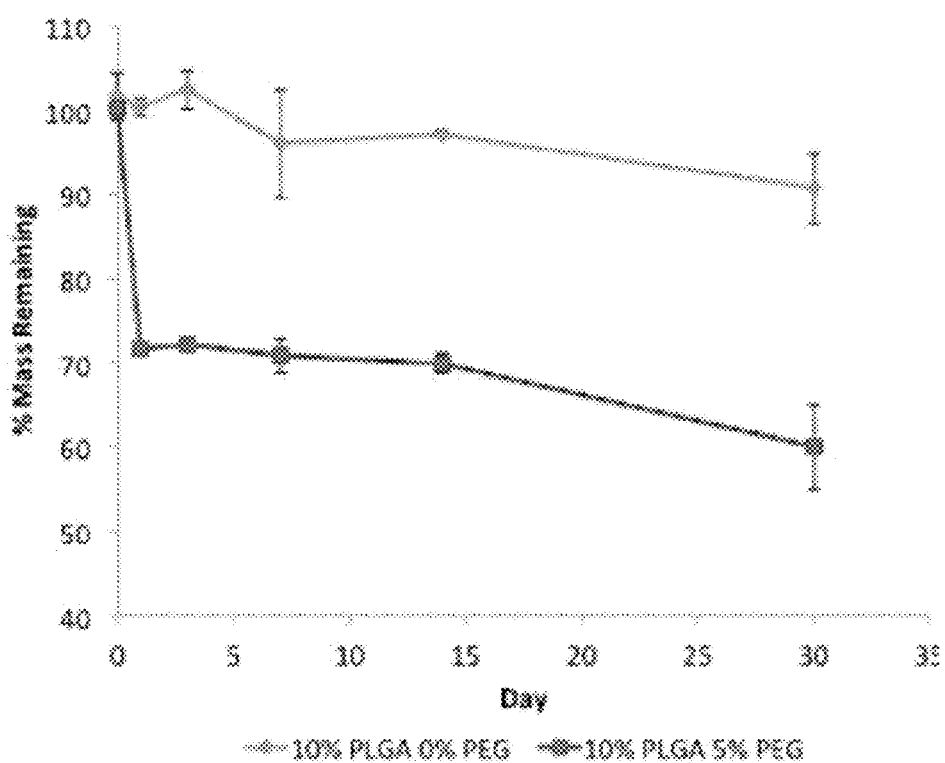
FIG. 8 illustrates graphically mass loss of 10% PLGA/0% PEG (wt/vol) versus 10% PLGA/5% PEG (wt/vol) (1× phosphate buffered saline (PBS) and pH 7.4) over a period of 30 days.
Figure 9:
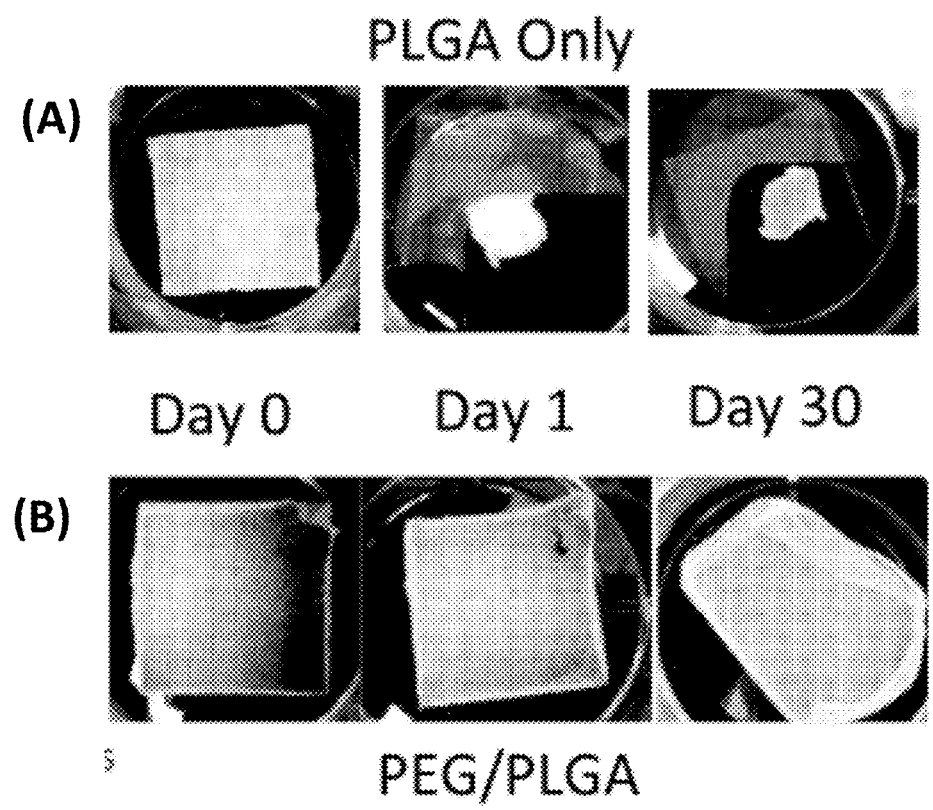
FIG. 9 are images showing mass loss and gross morphology change of a polymer mat formed from 10% PLGA/0% PEG (wt/vol) blend (Panel A), as compared to a polymer mat formed from 10% PLGA/5% PEG (wt/vol) blend (Panel B) at 0 days, 1 day and 30 days.

The blended polymers were also evaluated. Polymer blends including PEG were shown to have drastic effects on degradation, shape stability and morphology (FIGS. 8 and 9), as increased hydrophilicity can correlate with increased degradation (Makadia H. K. et al. (2011) "*Poly Lactic-co-Glycolic Acid (PLGA) as Biodegradable Controlled Drug Delivery Carrier*," Polymers 3:1377-97). These parameters are beneficial for predicting polymer sealant longevity in vivo.

Figure 10:
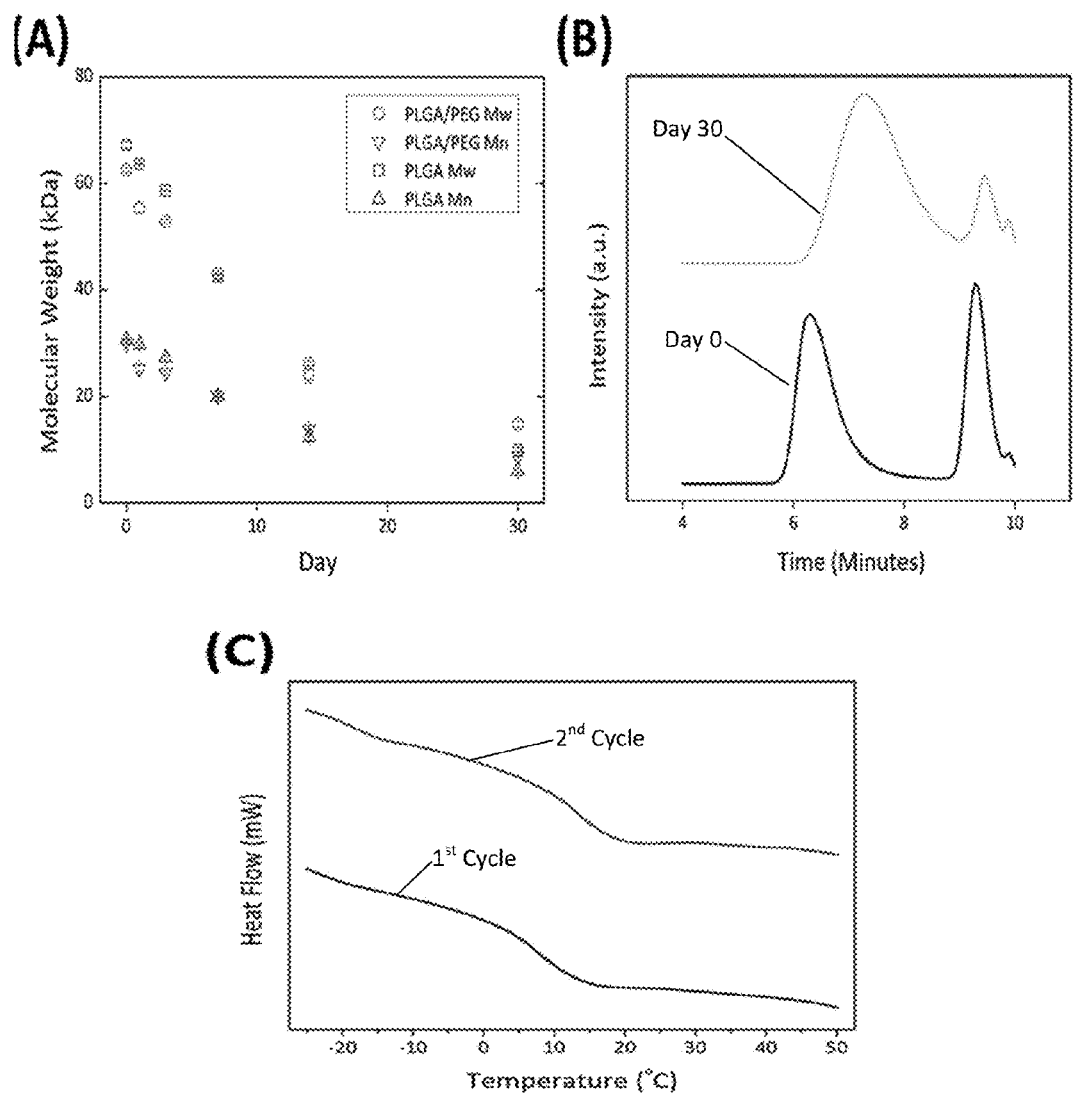
FIG. 10 illustrates number and weight average molecular weight corresponding to 10% PLGA (wt/vol)/0% PEG (wt/vol) and 10% PLGA (wt/vol)/5% PEG (wt/vol) solution blow spun samples (Panel A). Gel permeation chromatographs of a 10% PLGA (wt/vol)/5% PEG (wt/vol) sample at day 0 and day 30 of the in vitro degradation study show peaks representative of both PLGA and PEG at day 30 (Panel B). DSC of a 10% PLGA (wt/vol)/5% PEG (wt/vol) sample at day 30 shows the persistence of the plasticization effect of PLGA over the full time period ($T_g$ less than body temperature) (Panel C).

Number and weight average molecular weight corresponding to 10% PLGA (wt/vol)/0% PEG (wt/vol) and 10% PLGA (wt/vol)/5% PEG (wt/vol) solution blow spun samples were assessed (FIG. 10). The incorporation of PEG did not significantly impact the degradation rate of PLGA over 30 days in vitro (FIG. 10, Panel A). Gel permeation chromatographs of a 10% PLGA (wt/vol)/5% PEG (wt/vol) sample at day 0 and day 30 of the in vitro degradation study show peaks representative of both PLGA and PEG at day 30 (FIG. 10, Panel B). DSC of a 10% PLGA (wt/vol)/5% PEG (wt/vol) sample at day 30 shows the persistence of the plasticization effect of PLGA over the full time period ($T_g$ less than body temperature) (FIG. 10, Panel C).

In Vitro Biocompatibility

Cytotoxicity of the candidate materials is assessed through a combination of assays. A metabolic activity assay (MTS) with multiple cell lines (including L929 fibroblasts (L929) and human coronary artery endothelial cells (HCAEC)) was used to evaluate any associated cytotoxicity at 24 hours of both: (A) the direct deposition of polymer fibers onto cells; and (B) cells seeded onto polymer fiber mats. The polymer fibers were shown to have no or negligible effect on cell viability (FIGS. 15 and 16).

Figure 19:
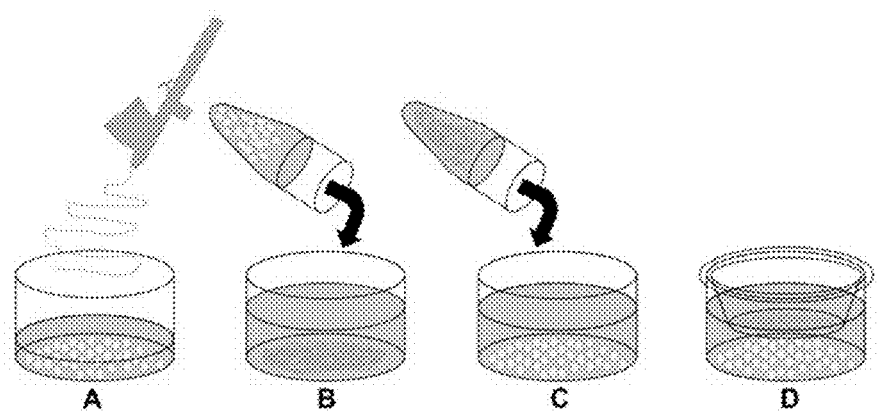
FIG. 19 is a schematic of an exemplary cell experimental design set up depicting: (A) deposition of polymer fibers, (B) cells seeded on fibers, (C) cells exposed to degradation product extract, and (D) indirect interaction using a transwell insert. These studies are utilized to assess biocompatibility through cell viability assays (e.g., L929 and HCAEC) and inflammatory response (PBMs).

Additional assays can be implemented to evaluate any associated cytotoxicity of: (C) degradation product extract; and (D) indirect cell cytotoxicity using trans-well inserts (FIG. 19). A similar experimental setup can be utilized with murine derived primary bone marrow macrophages (PBMs) where ELISA (IL-1, IL-6, IL-12, IL-10 and TNF alpha) determines cytokine activation and secretion to monitor inflammatory response (Walk R. M. et al. (2012) "*T-cell activation is enhanced by targeting IL-10 cytokine production in toll-like receptor-stimulated macrophages*," Imuno-Targets and Therapy 2012:1:13-23). Such studies can provide a quantitative measure of the effect of PLGA/PEG fiber deposition on cell viability and inflammatory response. Hemocompatibility can be assessed following ISO standard 10993-4 using whole human blood and plasma. Contact activation can be assessed through prothrombin time (PT), partial thromboplastin time (PTT), and Factor XII activation. Complement activation can be assessed through complement component assays for C3, C4, and C5a. Thrombin generation is monitored by thrombin-antithrombin (TAT) complex formation. Fibrinogen to fibrin conversion can be assessed through light microscopy, and fibrinolysis assessed through light microscopy and fibrinolysis through thrombin time. Hemolysis can be monitored by free hemoglobin assays. Finally, platelet activation can be assessed using light microscopy, scanning electron microscopy (SEM), spreading, CD 62 assays, and CD 63 assays.

Discussion

A catalog of solution conditions for solution blow spinning PLGA and PEG varying molecular weights, concentrations, and blends were characterized for morphologic and mechanical properties. Adhesive strength was demonstrated to be comparable or superior to commercial fibrin, glutaraldehyde, and other synthetic hydrogel based sealants. The direct deposition of polymer fibers through solution blow spinning was shown to have negligible effect on cell viability and function. In addition, in vitro characterizations of the disclosed materials is predictive of further in vivo biocompatibility and efficacy in clinically relevant animal models.

Balancing mechanical strength, adhesive strength, and the ability to generate polymer fibers is attained by blending polymer molecular weight of two polymers. As shown in FIG. 20, the ability to modulate the resulting morphology of solution blow spun polymer solutions is achieved through the use of blends of varying molecular weight. Tissue adhesive strength may also be further modulated utilizing several functionalization strategies, as described in further detail below.

With regard to shelf-stability, diminished material adhesiveness over time is not expected, although storage under vacuum or inert atmosphere may be implemented if desired. However, storage testing of the materials has not suggested such additional storage considerations are necessary (e.g., no change in material morphology or adhesive strength was displayed after storage for more than 1 month as a solution at ambient conditions).

With regard to biocompatibility considerations, non-degradable polymers have the potential to cause harm if inhaled, and most volatile solvents are too toxic for direct application. Solvents other than acetone may be utilized, such as for example ethyl acetate. Ethyl acetate is commonly used in perfumes and is present in fruits and wines. Additional solvents exhibiting suitable biocompatibility may be identified by accelerating evaporation rate through heating, through utilization of additional $CO_2$ flow or via a vacuum (exhaust system). However, while the use of acetone may not be suitable for all applications, the cell viability data obtained demonstrates that acetone quickly evaporates and thus the amount reaching the cell surfaces is minimal (FIG. 16). Additionally, for polymer fibers to be generated and maintained, any solvent utilized will evaporate from the system. Thus, the utilization of acetone does not adversely impact biocompatibility. Moreover, acetone based sealants and adhesives are widely used and proven safe in dental applications (Ritter A. V. et al. (2009) "*An eight-year clinical evaluation of filled and unfilled one-bottle dental adhesives*," J. Am. Dent. Assoc. 140:28-37; Kersten S. et al. (2001) "*Fissure sealing: optimization of sealant penetration and sealing properties*," Am. J. Dent. 14:127-31). Thus, the utilization of acetone does not pose any biocompatability concerns, consistent with the findings herein.

Polymer Functionalization

Polymer functionalization chemistries are implemented for improving or optimizing adhesive strength, material strength and/or fiber generation of the polymer constructs formed by solution blow spinning. Functionalization may be confirmed with H-NMR and IR spectroscopy. Material properties are characterized through peel, shear, wound closure, and tensile tests. Additionally, cell viability, inflammatory response, and hemocompatibility assays may be utilized to assess biocompatibility of the chemically modified polymer constructs.

The disclosed PLGA/PEG blends may thus be further enhanced or modified for some biomaterial applications or clinical conditions. The desired characteristics depend on the particular material application, for example as a low-pressure tissue sealant (e.g., intestinal applications), an intermediate pressure sealant (e.g., lung applications), or a high-pressure hemostatic agent (e.g. vascular applications). In some implementations, functionalization is accomplished through end group functionalization or aminolysis of PLGA (Zhu Y. et al. (2013) *Aminolysis-based surface modification of polyesters for biomedical applications*," Rsc. Advances 3:2509-19). In some implementations, PEG is also modified to have reactive end groups for improved adhesive strength (Harris J. M. (1985) "*Laboratory Synthesis of Polyethylene-Glycol Derivatives*," J. Macromol. Sci.—Reviews in Macromolecular Chemistry and Physics C25:325-73).

In one implementation, PLGA is functionalized with oxidized dextran (ODEX). ODEX has been investigated as a platform material for adhesive hydrogels and coatings, and is shown to be biocompatible (Maia J. et al. (2005) "*Synthesis and characterization of new injectable and degradable dextran-based hydrogels*," Polymer 46:9604-14; Mandavi A. et al. (2008) "*A biodegradable and biocompatible gecko-inspired tissue adhesive*," PNAS USA 105:2307-12; Li H. B. et al. (2011) "*Photocrosslinkable tissue adhesive based on dextran*," Carbohydrate Polymers 86:1578-85). While it has advantageous wet adhesive properties, mechanical properties and solubility characteristics of ODEX restrict its utility for some applications. However, the additive value of using ODEX-PLGA allows for a balance of mechanical and adhesive strength.

Figure 21:
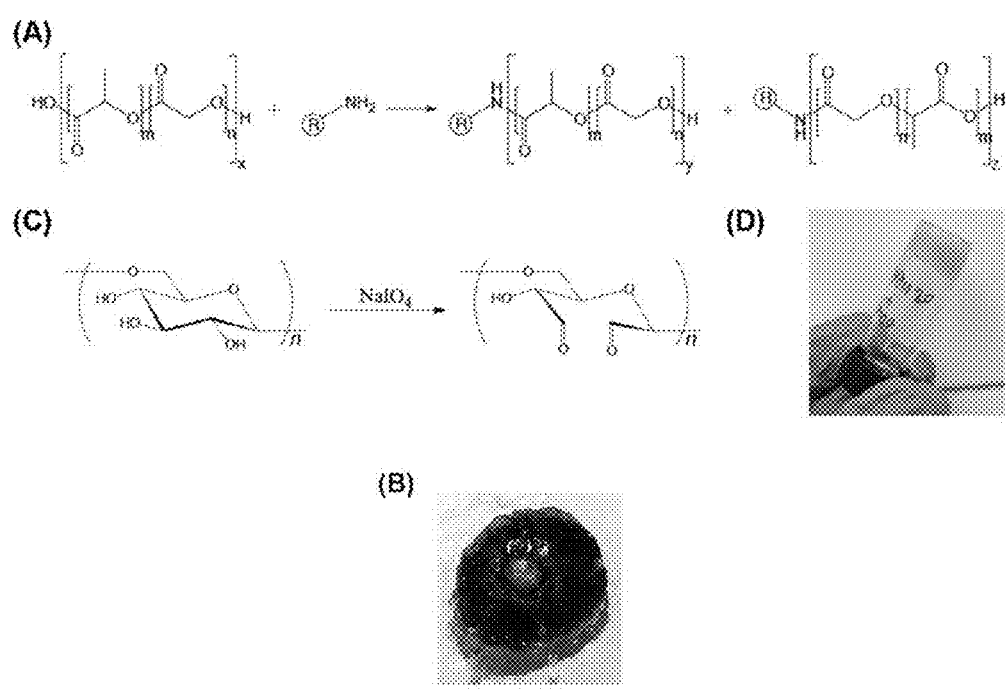
FIG. 21 illustrates functionalization schemes of PLGA. Panel A depicts aminolysis reaction schematic for the functionalization of PLGA. Panel B depicts ninhydrin stain (purple) showing the presence of primary amines after the reaction of PLGA with hexamethylene diamine Panel C depicts oxidation reaction schematic of dextran with sodium periodate. Panel D is an image showing gel formation of oxidized dextran in the presence of a multifunctional primary amine-containing compound.
Figure 22:
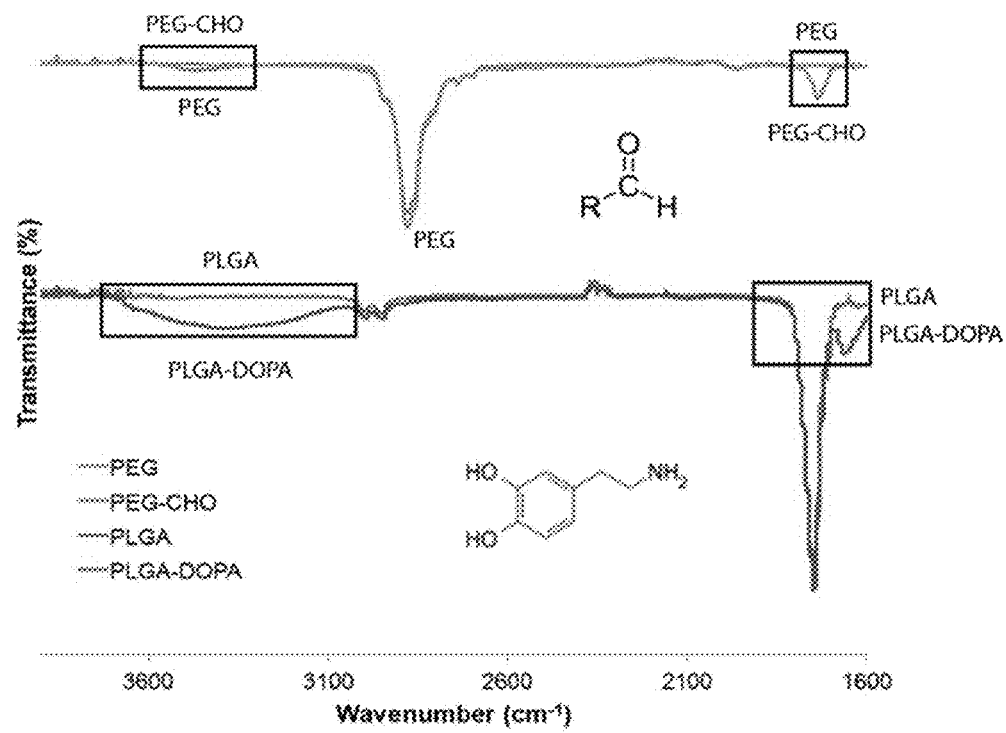
FIG. 22 illustrates Fourier transform infrared spectroscopy (FTIR) data of PEG, aldehyde (CHO) functionalized PEG, PLGA and dopamine (DOPA) functionalized PLGA. Aldehyde functionality imparts reactivity towards thiols and amines contained in tissue. Dopamine introduces catechol functionality that reacts with primary amines and sulfur groups present in tissue through Michael addition and Schiff base reaction.

Functionalization of PLGA may be accomplished via aminolysis and oxidation chemistry (FIG. 21). Synthesis of ODEX-PLGA is alternatively accomplished using EDC chemistry (Jeong Y. I. et al. (2011) "*Doxorubicin-incorporated polymeric micelles composed of dextran-b-poly(DL-lactide-co-glycolide) copolymer*," Internat. J. Nanomed. 6). In another implementation, PLGA is modified with catechol functionality. Catechol groups mimic naturally occurring wet adhesives found in marine mussels (Lee B. P. (2011) "*Mussel-Inspired Adhesives and Coatings*," Annu. Rev. Mater. Res. 41:99-132), and can be incorporated into PLGA through EDC chemistry or aminolysis (FIG. 22).

In some implementations, PEG end group modification with aldehydes (FIG. 22) and/or N-hydroxysuccinimide (NHS) is provided for enhancing tissue adhesion. PEG end group functionalization may be accomplished in various ways. In one implementation, hydroxyl groups are converted to aldehydes via Albright-Goldman oxidation with dimethyl sulfoxide and acetic anhydride (Albright J. D. et al. (1967) "*Dimethyl Sulfoxide-Acid Anhydride Mixtures for Oxidation of Alcohols*," J. Amer. Chem. Soc. 89:2416). In another implementation, hydroxyl groups are first converted to carboxylic acids via reaction with succinic anhydride and trimethylamine (Chittasupho C. et al. (2009) "*ICAM-1 targeting of doxorubicin-loaded PLGA nanoparticles to lung epithelial cells*," European J. Pharmaceut. Sci. 37:141-50). This allows for subsequent reaction with either N,N'-Dicyclohexylcarbodiimide (DCC) or 1-Ethyl-3-(3-dimethylaminopropyl) carbodiimide (EDC) and NHS. Either functionalization approach imparts reactivity towards thiols and amines contained in tissue. Functionalization is confirmed with FTIR and H-NMR.

PEGs of varying molecular weights and chain architectures (1 kDa-10 kDa, linear, 4-arm, 8-arm) are also investigated for their ability to be solution blow spun when incorporated into optimally performing PLGA/PEG blends. Different molecular weights and chain architectures alter the functional group density in the resulting polymer blends. Additionally, different end group conversions are shown for 1K PEG (84%) and 10K 8-arm PEG (42%) using the Albright-Goldman oxidation, as quantified with H-NMR.

In one implementation, PLGA is first functionalized through aminolysis with hexamethylene diamine or PEG-amine to create primary amine terminated PLGA, and confirmed with FTIR. ODEX is synthesized through oxidation of dextran, which imparts aldehyde functionality. The modification is confirmed by FTIR and percent conversion of hydroxyl groups to aldehydes determined by H-NMR. PLGA-amine and ODEX are combined in varying ratios to create PLGA-block-ODEX and ODEX-branch-PLGA. In addition, molecular weights and molecular weight ratios of PLGA and Dextran are varied. In another implementation, PLGA is modified with dopamine through aminolysis. This modification is confirmed with FTIR and H-NMR. Morphology is characterized by SEM.

In another implementation, PLGA may be modified to contain an antibiotic agent. Such modification is particularly suitable in applications involving a relatively high risk of infection (e.g., such as for treating open wounds and/or burn wounds). The modified polymer fiber construct acts as an effective hemostatic agent, sealing the wound while also simultaneously killing or inhibiting any bacterial growth in the treated area.

The resulting polymers are assessed for solubility in suitable solvents and solvent mixtures for solution blow spinning. These polymers are then incorporated into PLGA/PEG blends exhibiting desired characteristics, including their ability to be solution blow spun. Solution and deposition conditions for blow spinning may additionally be adjusted for attaining optimal material properties as desired for a particular application. Chemically functionalized polymer constructs are tested for adhesive strength and in vitro biocompatibility, with the best in vitro performing materials utilized for in vivo applications.

In Vivo Studies in Acute and Chronic Pre-Clinical Models

Vertebrate animals were utilized for in vivo evaluation of medical sealant efficacy, biocompatibility and degradation of the disclosed blow spun polymer sealants. The in vivo experimentation tests the effects of the disclosed sealant materials under realistic conditions accurately represent human applications. All animal experiments and care were approved by the Institutional Animal Care and Use Committee (IACUC) of Children's National Medical Center in accordance with the "*Guide for the Care and Use of Laboratory Animals*" published by the National Institutes of Health (National Institutes of Health publication 85-23, revised 1996).

C57BL/6 Mice, 1-6 months old and of either sex, were used for intramuscular implant model and cecal intestinal anastomosis model. The mouse was selected for some studies given it is a small and relatively inexpensive animal model, while large enough to reliably perform an intramuscular implant for assessing biocompatibility. Yorkshire piglets between 5-8 kg, 4-6 weeks old and of either sex, were used for surgical sealant efficacy studies. Intestinal anastomosis models were used to quantify bursting pressure strength of the site of anastomosis and to evaluate surgical efficacy and biocompatibility. The piglet was selected because it has comparable intestine size to that of a child, and thus more accurately represent human physiology compared to a murine model (Morten A. et al. (2006) "*Animal models in pediatric surgery*," Pediatric Surgery International 22(2):111-28). The piglet model therefore has efficacy implications for infants and children, who may benefit significantly from the disclosed materials and methodologies. The number of animals utilized provide for suitable sample sizes for statistical assessment (power analysis and t-test) to determine the meaningful difference in independent variables and outcomes for achieving the objectives herein.

Standard aseptic procedures were used for all animal experimentation. During and after administration of anesthetics, mice were monitored for response to pain stimuli by toe or skin pinch. Once anesthetic depth was achieved and no response to stimulus observed, procedures were commenced. If a response was observed during surgery, the procedure was stopped and additional anesthesia administered. Animals were monitored post operatively for signs of distress and sick mouse posturing. The term "sick mouse posturing" is used to describe symptoms such as ruffled fur, piloerection, and increased respiratory rate. Mice exhibiting these signs were given appropriate pain medication in the event that they are experiencing discomfort. During experimentation, monitoring of mice continued every 2 hours and for an additional 6 hours and every day afterwards. Animals were given buprenorphine every 8-12 hours or butorphanol every 46 hours postoperatively for pain or discomfort. During the piglet procedures, the piglet's color, pulse, and movement were monitored in order to ensure adequate anesthesia. Pulse and oxygen saturation were monitored using a pulse oximeter attached to the piglet's ear.

Mice were euthanized by $CO_2$ and cervical dislocation, consistent with AVMA Guidelines for the Euthanasia of Animals (AVMA 2013.01:48-51, 60-61). Piglets were euthanized by intravenous injection of barbiturates, consistent with AVMA Guidelines for the Euthanasia of Animals (AVMA 2013.01:48-51, 60-61). After the animal was euthanized, the body underwent a necropsy, wherein tissue specimens were collected for histological and immunohistochemical analysis and flow cytometry. After the necropsy was completed, incisions were closed.

In vivo pre-clinical studies of safety and efficacy of disclosed biomaterials in animal models are divided into acute (non-survival) and chronic (survival) studies in both small (mouse) and large (piglet) animal models. The studies were performed to evaluate safety and efficacy of the deposited solution blow spun polymer sealants in specific surgical applications in the pre-clinical animal models. In addition, the blow spun sealants were compared to commercial fibrin, glutaraldehyde, and synthetic hydrogel based sealants.

Using acute studies, the burst pressure of reinforced intestinal anastomoses as well as the peak airway pressure tolerated in lung resections sealed with polymer through the proposed technique was determined. The ability of blow spun polymers to tamponade venous bleeding in the liver as well as venous and arterial bleeding following direct vascular injury was also determined. Further, the ability of the polymer materials to aid in aortic anastomosis was assessed. Using chronic models, the biocompatibility and longevity of the polymer constructs for use sealing intestinal anastomosis, lung resection surface, and abdominal aortic anastomosis was determined Histopathologic study and immune cell infiltrate were evaluated by cellular and immunologic studies, and sealant longevity assessed.

In the acute non-survival studies, animals were used to investigate the applications of the disclosed materials and techniques. Each animal was used for multiple procedures, bowel anastomoses, lung resections, liver lacerations, liver segmental resection, femoral vessel injuries, and/or abdominal aortic anastomosis. Each animal received several but not all procedures, with each acute study procedure repeated at least three times amongst the tested animals. Additional animals were used to assess the best performing sealants as determined in other assessments. The outcome of these procedures in the acute studies was utilized to guide the choice of procedures in the chronic studies. The chronic models were used to further assess biocompatibility and long-term procedural outcomes. Animals were used in the chronic studies involving intestinal anastomosis and lung resection, and in chronic studies involving abdominal aortic anastomosis.

Figure 23:
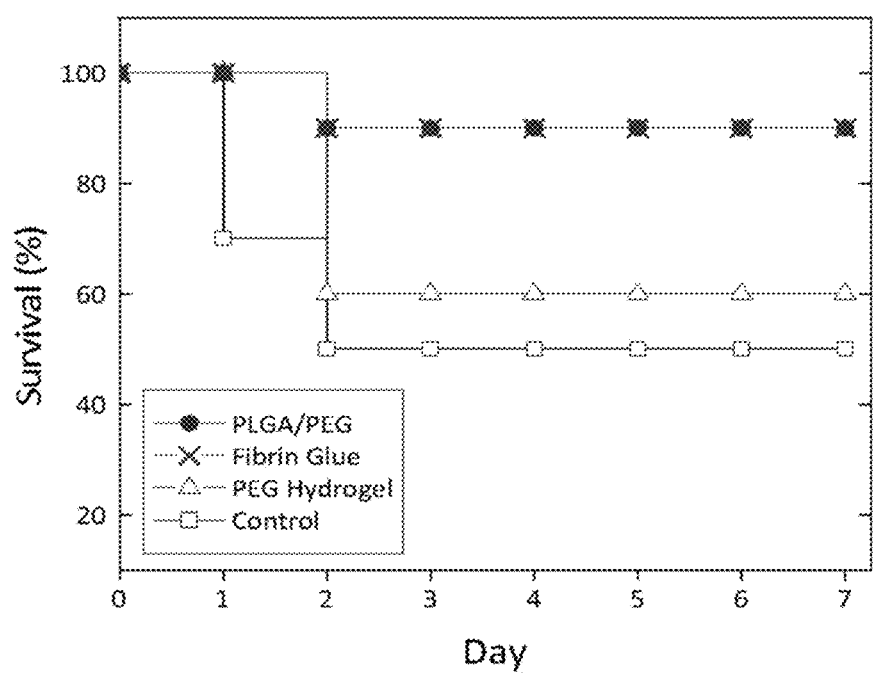
FIG. 23 illustrates graphically data obtained from cecal anastomosis survival studies. As shown, 50% of a 4 suture control group died by day 3 due to complications such as leakage at the anastomosis (n=10). In contrast, 10% of the 4 suture anastomosis supplemented with solution blow spun PLGA/PEG leaked, with 9 out of 10 mice surviving the 7 day study (n=10).

The intestinal anastomosis surgical model was selected because of the high prevalence of anastomotic leak in the gastrointestinal tract post-surgery and the high rate of mortality when complications occur (Bruce J. et al. (2001) "*Systematic review of the definition and measurement of anastomotic leak after gastrointestinal surgery*," Br. J. Surg. 88:1157-68). For example, ccomplications may arise from ischemia of the bowel at the anastomosis, or from technical failure (misplaced suture) by the surgeon (Brisinda G. et al. (2009) "*Colonic anastomotic leak: risk factors, diagnosis, and treatment*," J. Am. Coll. Surg. 208:1152-3). Although such problems have led to the investigation of the use of surgical sealants as a means of supplementing traditional sutures or staples, the use of conventional sealants has resulted in very limited improvements in operational outcomes. Indeed, the use of such conventional sealants has even resulted in decreases in survival rates as compared to a suture only control in animal models (Slieker J. C. et al. (2013) "*Prevention of leakage by sealing colon anastomosis: experimental study in a mouse model*," J. Surg. Res. 184:819-24). In contrast, the PLGA/PEG sealants of the present invention demonstrated an increase in survival rates by 60% or more over a suture only control in a high-risk anastomosis model (FIG. 23).

Mouse Intramuscular Implant Model

An intramuscular implant model was utilized for the initial biological evaluation of direct deposition PLGA/PEG solution blow spun surgical sealants that exhibited preferred in vitro performance and characteristics. The intramuscular implantation model was chosen for initial studies because it is sensitive for assessing biocompatibility due to increased vascularization and the model's wide applicability across multiple procedures.

Mice used in each experimental group underwent histology, or sites harvested for flow cytometry to evaluate cell infiltrate. Both hind legs were used, with the opposite hind leg serving as an internal sham control, thereby minimizing the number of animals used. The sites were closed with vicryl sutures. The fibrin, glutaraldehyde, and synthetic hydrogel based sealants were used in the same manner for comparison. At time points of 1 day and 7 days, mice were sacrificed and the implantation and sham site excised and prepared for histological analysis (n=3) and flow cytometry (n=3). These time points were altered to match the degradation profile predicted by the in vitro degradation studies, and encompass the full degradation cycle of the blow spun sealant material.

Figure 24:
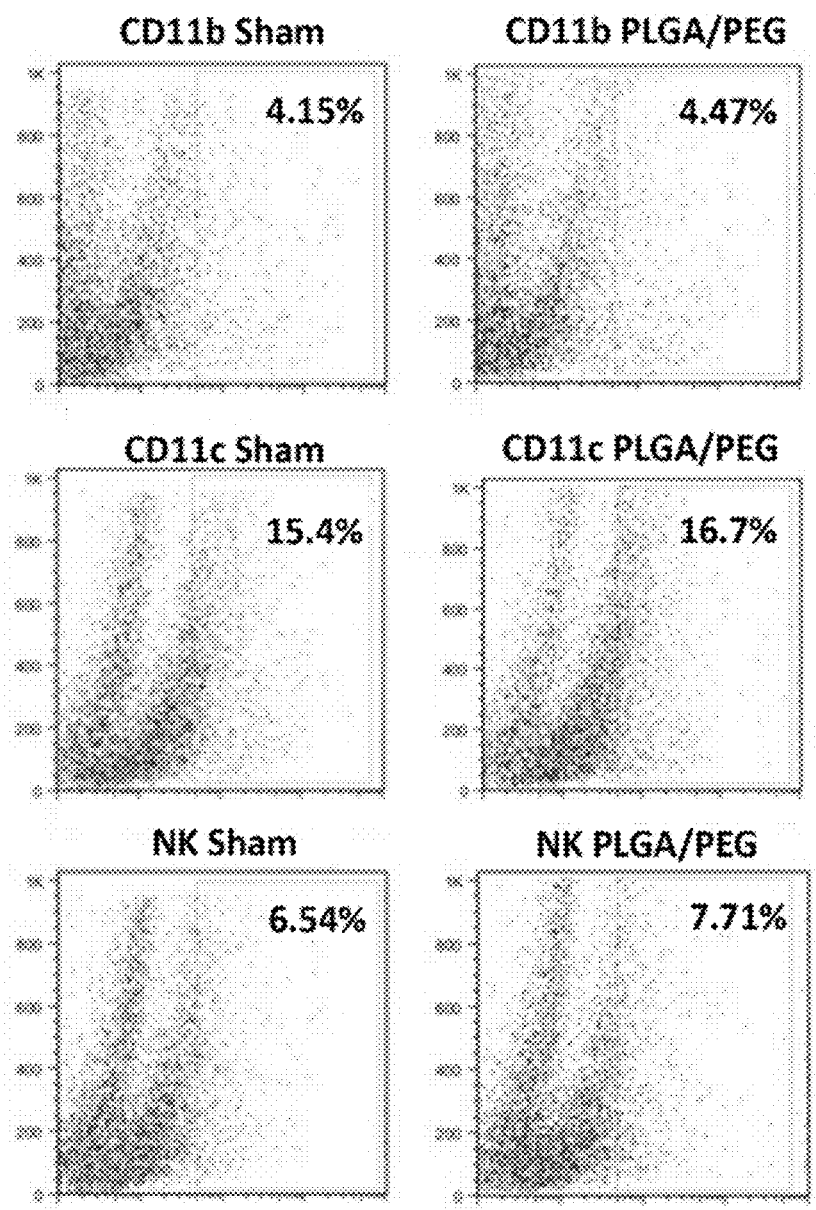
FIG. 24 depicts representative flow cytometry data from an intramuscular implantation model of a sham procedure and PLGA/PEG at day 7.

Histological evaluation was used to determine the extent of fibrosis, degeneration, distribution of inflammatory cell types as a function of distance, necrosis, fatty infiltrate, material remnants/degradation, as well as the quantity and quality of tissue ingrowth. Appropriate staining (e.g., hematoxlyin and eosin), was used to visualize these parameters. Additionally, flow cytometry was used to quantify any elevations in certain cell populations that are indicative of an inflammatory response (Leukocytes (CD45+), T cells (CD4 and CD8+), NK cells (NK1.1+), macrophages (CD11b+) and dendritic cells (CD11c+)) (FIG. 24). This was accomplished through site specific tissue digestion and cell type specific immuno-histochemical staining.

Mouse Cecal Intestinal Anastomosis Model

Figure 25:
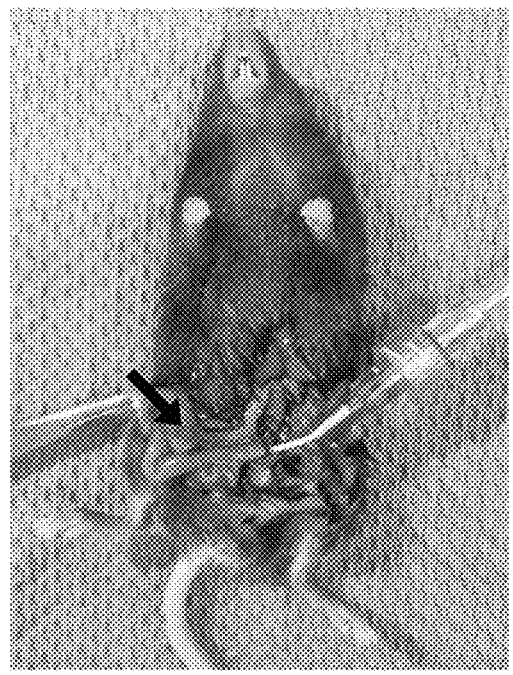
FIG. 25 is an image of a mouse being prepared for burst pressure experimentation.

Solution blow spun PLGA/PEG polymer blends for use as a surgical sealant in an intestinal anastomosis model was demonstrated. 16-week old C57BL6/J mice were anesthetized using 100 mg/kg and 10 mg/kg xylazine. An exploratory laparotomy incision was made, and the cecum was exposed. The cecum was transected, leaving the mesenteric sidewall intact in order to preserve the blood supply. The cecum was then re-anastomosed using 4 interrupted 7-0 vicryl sutures (FIG. 25). 40 anastomoses were performed on 40 mice with 10 mice in each of 4 groups (n=10). The groups included a control group that underwent the sutured anastomosis without any additional sealant and 3 experimental groups that underwent the sutured anastomosis and received additional sealant. These groups were supplemented with either solution blow spun 10% PLGA (wt/vol)/5% PEG (wt/vol) sprayed directly on the suture site, Coseal (PEG hydrogel, Baxter International Inc.), or Tisseel (Fibrin glue, Baxter International Inc.). The commercial sealants were prepared and applied to the anastomoses in accordance to the product insert directions. Following a set time of 2 minutes for all groups, the bowel was placed into the abdomen and the skin was closed using a 4-0 vicryl suture in a running fashion. All surgeries were performed by one surgeon who was blinded to the treatment groups. Loupes were used for magnification in all cases.

Each animal was weighed preoperatively, and weights were taken every other day until day of sacrifice. Animals were allowed to survive for 7 days and were sacrificed after necropsy and harvestation of the anastomotic bowel segment. Animals were monitored daily and were sacrificed prior to 7 days if they showed signs of extreme distress due to sepsis. Necropsy was performed to determine the cause of sepsis or death.

A cecal intestinal anastomosis mouse model was used to assess the clinical potential of this material. This type of procedure can be technically challenging and suffers from high rates of morbidity and mortality when complications of leakage occur. A high-risk model was adapted from other groups in which a sub-clinical number of sutures leads to increased incidence of mortality. The solution blow spun 10% PLGA/5% PEG sealant was used to supplement the sutures. Performance was compared to a suture-only control, and the sutures supplemented with a commercially available fibrin glue or PEG hydrogel sealant.

Figure 26:
FIG. 26 is another image of the mouse of FIG. 25, and showing resistance to burst by PLGE/PEG supplemented anastomosis.
Figure 27:
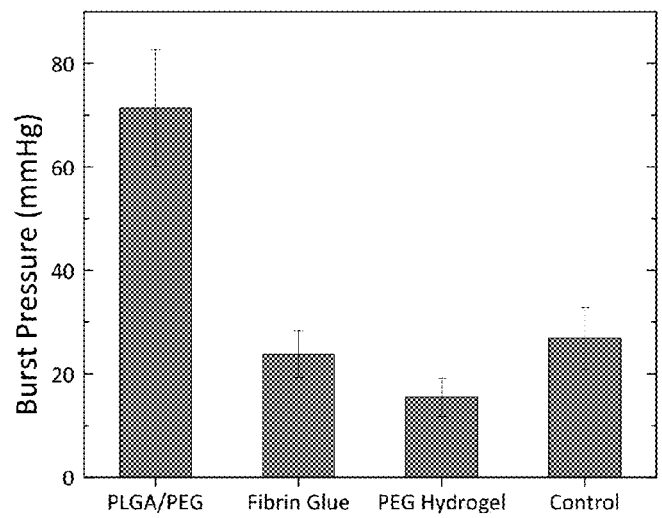
FIG. 27 illustrates graphically data from burst pressure experimentation. Bars represent standard error.

In an initial study, burst pressure at the site of anastomosis was measured at 24 hours (FIG. 27). The PEG/PLGA sealant supplemented sutures were exceptionally resistant to leakage. At 24 hours, blow spun PLGA/PEG sealant reinforced cecal anastomosis had an average burst pressure of 71.4 mmHg (n=6); blow spun PLGA/PEG sealant reinforced with the fibrin glue had an average burst pressure of 23.8 mmHg (n=5); blow spun PLGA/PEG reinforced with the PEG hydrogel sealant had an average burst pressure 15.5 mmHg (n=4); suture only control had an average burst pressure of 26.9 mmHg (n=5) (FIG. 27). The intestine completely fills with fluid, and significantly swells before any minor leakage occurs (FIG. 26). This is in contrast to the other 3 groups tested that had an average burst pressure that was over three times lower the solution blow spun PLGA/PEG sealant.

The same cecal intestinal anastomosis model was used in a 7-day survival study (FIG. 23). Cecal intestinal anastomosis survival data is presented in the table below:

| Animal | Days Survived[a] | Initial Weight [g] | Final Weight [g] | Outcome |
| --- | --- | --- | --- | --- |
| PLGA/PEG 1 | 7 | 20 | 19 | Healthy |
| PLGA/PEG 2 | 7 | 19 | 19 | Healthy |
| PLGA/PEG 3 | 7 | 20 | 19 | Healthy |
| PLGA/PEG 4 | 7 | 19 | 18 | Healthy |
| PLGA/PEG 5 | 7 | 21 | 20 | Healthy |
| PLGA/PEG 6 | 7 | 20 | 17 | Healthy |
| PLGA/PEG 7 | 2 | 20 | 19 | Bowel perforation |
| PLGA/PEG 8 | 7 | 22 | 20 | Healthy |
| PLGA/PEG 9 | 7 | 21 | 20 | Healthy |
| PLGA/PEG 10 | 7 | 20 | 18 | Healthy |
| Fibrin Glue 1 | 7 | 19 | 17 | Healthy |
| Fibrin Glue 2 | 7 | 20 | 20 | Healthy |
| Fibrin Glue 3 | 7 | 21 | 20 | Healthy |
| Fibrin Glue 4 | 2 | 22 | 19 | Bowel perforation |
| Fibrin Glue 5 | 7 | 18 | 17 | Healthy |
| Fibrin Glue 6 | 7 | 19 | 18 | Healthy |
| Fibrin Glue 7 | 7 | 20 | 18 | Healthy |
| Fibrin Glue 8 | 7 | 18 | 19 | Healthy |
| Fibrin Glue 9 | 7 | 19 | 17 | Healthy |
| Fibrin Glue 10 | 7 | 20 | 19 | Healthy |
| PEG Hydrogel 1 | 7 | 22 | 19 | Healthy |
| PEG Hydrogel 2 | 7 | 23 | 20 | Healthy |
| PEG Hydrogel 3 | 7 | 20 | 18 | Healthy |
| PEG Hydrogel 4 | 7 | 20 | 13 | Walled off abscess[b] |
| PEG Hydrogel 5 | 2 | 20 | 18 | Bowel perforation |
| PEG Hydrogel 6 | 2 | 20 | 18 | Bowel perforation |
| PEG Hydrogel 7 | 7 | 22 | 19 | Healthy |
| PEG Hydrogel 8 | 2 | 19 | 17 | Bowel perforation |
| PEG Hydrogel 9 | 2 | 19 | 17 | Bowel perforation |
| PEG Hydrogel 10 | 7 | 20 | 20 | Healthy |
| Control 1 | 2 | 19 | 19 | Bowel perforation |
| Control 2 | 7 | 19 | 18 | Healthy |
| Control 3 | 7 | 21 | 20 | Healthy |
| Control 4 | 1 | 19 | 18 | Bowel perforation |
| Control 5 | 2 | 20 | 19 | Bowel perforation |
| Control 6 | 1 | 21 | 19 | Ischemia |
| Control 7 | 1 | 20 | 19 | Ischemia |
| Control 8 | 7 | 20 | 17 | Healthy |
| Control 9 | 7 | 20 | 19 | Healthy |
| Control 10 | 7 | 20 | 28 | Healthy |

As noted previously, the sub-clinical number of suture used in this model cause a high incidence of complication. Namely, bowel perforation, ischemia, obstruction, and sepsis. This is reflected in the suture-only control resulting in a 50% mortality rate over this 7-day time period, with all deaths occurring before day 3. The sutures supplemented with the PEG hydrogel sealant saw a similar mortality rate at 60%. One mouse from this group survived the 7 days but failed to thrive. This was characterized by weight loss and the observation of a walled off abscess during necropsy. In contrast, the use of either the solution blow spun PLGA/PEG blend sealant and the fibrin glue resulted in a 10% mortality rate, representing a 40% improvement over the suture-only control.

Piglet Models

Anesthetized piglets were used in which the animals were ventilated, continuously hydrated and maintained in a euglycemic state with intra-venous fluids, and monitored throughout experimentation in accordance with prescribed institutional standards. Oxygen saturation and blood pressure were continuously measured. In these acute studies, the effect of the proposed blow spun sealant was determined on intestinal anastomosis, lung resection, liver injury and resection, abdominal aortic anastomosis, and its ability to control venous and arterial bleeding. At completion of the studies, the animals were euthanized from deep anesthesia.

Piglet Small Bowel Anastomosis Model

Figure 28:
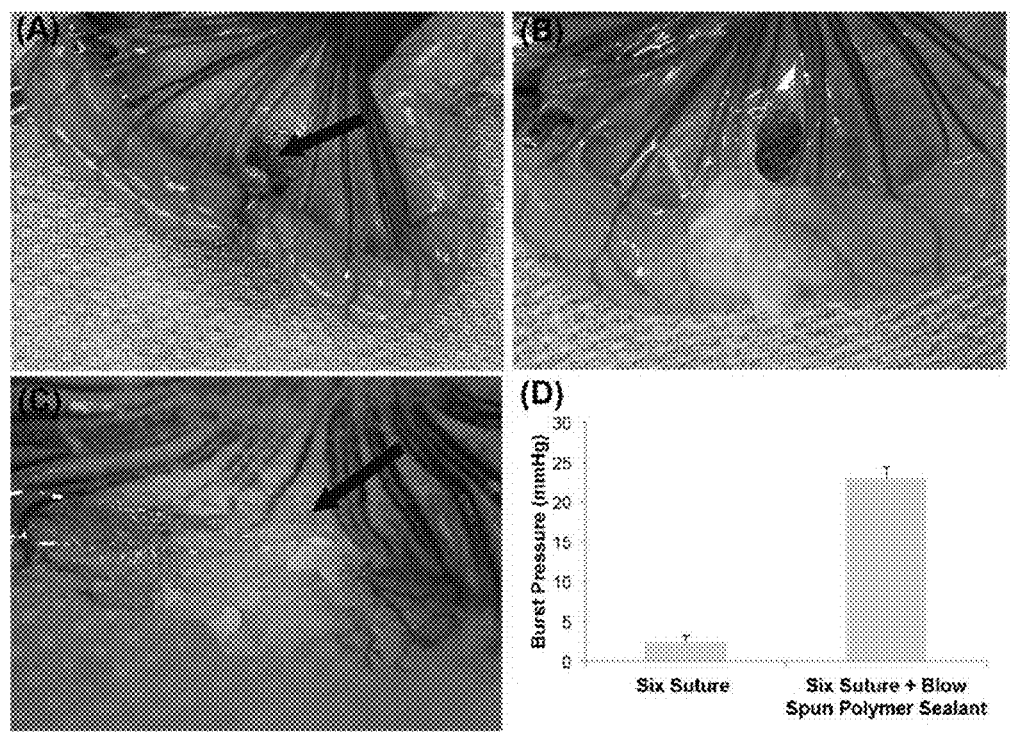
FIG. 28 illustrates burst pressure experimentation measured in isolated small bowel segments in non-survival piglet studies. An unprotected six suture anastomosis leaked at an average pressure of 2.5 mmHg (Panel A), while the same anastomosis sealed with blow spun polymer leaked at an average pressure of 23 mmHg (Panel B). In addition, the ability to bridge mesenteric defects created during an anastomosis procedure is illustrated (identified by arrows in Panels A and C). This is an important feature of the disclosed methodologies given defects are typically closed with sutures that can impair blood supply to the anastomosis, resulting in anastomotic break-down. Differences in burst pressure are shown graphically in Panel D (n=2).

A small midline laparotomy was performed and short segments of the jejunum isolated. An end-to-end anastomosis was performed with 6 Vicryl (PLGA) 4/0 sutures. The segment was isolated between clamps and a triple lumen catheter placed proximal to the anastomosis. One lumen was used for infusion and the other connected to a pressure transducer to determine intra-luminal bursting pressure (FIG. 28). The isolated segment was slowly infused with saline until leakage was noted at the anastomosis. Subsequently, the same anastomosis was sealed with the direct deposition of the blow spun polymer and the bursting pressure determined.

Piglet Liver Resection Model

Figure 29:
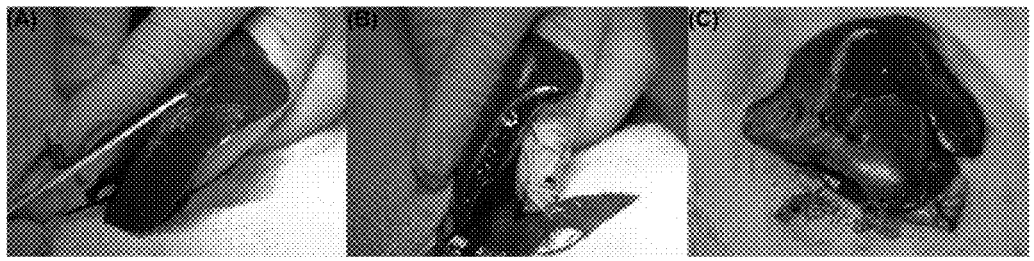
FIG. 29 are images from a liver resection piglet model. The edge of the right lobe of the liver was sharply excised (Panels A and B) and two mattress sutures were applied to slow blood loss. No hepatic vascular control was obtained prior to resection. The surface of the resection margin was sprayed with blow spun polymer. Complete vascular control at the resection margin was obtained and after 30 minutes of observation there was no evidence of bile leak or bile staining (Panel C).

The abdomen was opened and the liver exposed. The edge of the right lobe of the liver was sharply incised (FIG. 29, Panels A and B) and two mattress sutures were applied to slow blood loss. No hepatic vascular control was obtained prior to resection. The surface of the resection margin was sprayed with blow spun polymer and the efficacy of the polymer to tamponade bleeding from the liver surface determined and quantified by time to hemostasis. Complete vascular control at the resection margin was obtained and after 30 minutes of observation there was no evidence of bile leak or bile staining (FIG. 29, Panel C).

Piglet Femoral Artery Injury Model

Figure 30:
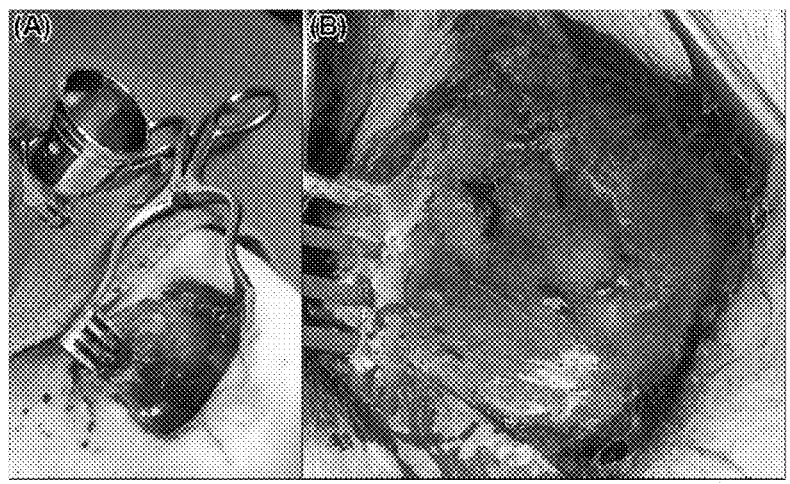
FIG. 30 are images from a femoral artery injury piglet model. After exposing the femoral artery, femoral vessel bleed was induced by scalpel (Panel A). PLGA/poly(ethylene glycol) blend fibers were deposited via solution blow spinning to form a fully conformal polymer matrix (Panel B). Arterial bleeding was stopped following polymer fiber deposition. Upon removal of the polymer matrix no residual bleeding was observed.

The femoral artery was exposed via incision and arterial bleeding induced by scalpel. PLGA/PEG polymer blend was applied to the injury via solution blow spinning, forming a fully conformal polymer matrix (FIG. 30) which sealed the injury and stopped arterial bleeding upon deposition. Upon removal of the polymer matrix, no residual bleeding was observed.

Additional Polymer Fiber Matrix Depositions in Piglet Model

Figure 31:
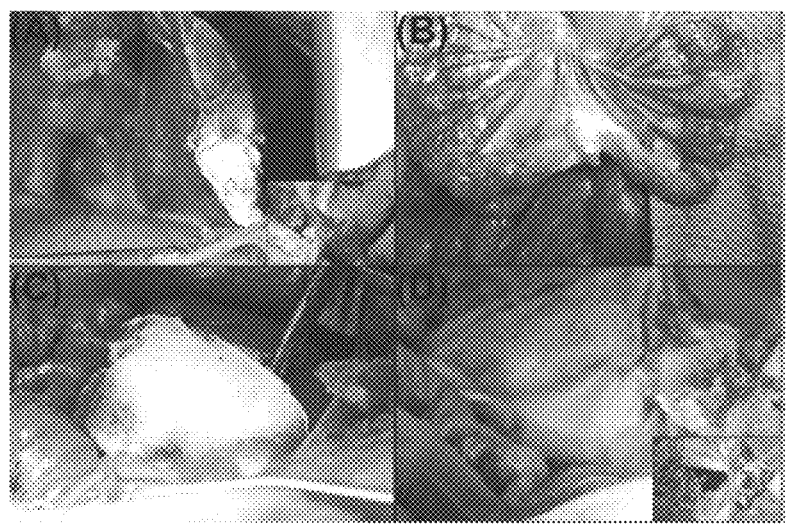
FIG. 31 illustrates conformal PLGA polymer fiber deposition and coating of: lung resection (Panel A); intestinal anastomosis (Panel B); liver laceration (Panel C); and diaphragmatic hernia (Panel D).

To demonstrate additional applications of the disclosed materials and method, PLGA fiber mats were directly deposited via solution blow spinning in multiple surgical models in a single piglet animal model. These include lung resection (FIG. 31, Panel A), intestinal anastomosis (FIG. 31, Panel B), superficial liver injury (FIG. 31, Panel C), and diaphragmatic hernia (FIG. 31, Panel D). In all cases, a conformal layer of fibers formed over the defect in less than 1 min. Visual observation by a surgeon confirmed that PLGA fiber deposition stopped the liver bleeding and air leakage from the lung surface following segmentectomy.

Discussion

The blow spun polymer sealants demonstrated excellent sealing capabilities and without any toxicity issues for any test or model. Thus, the disclosed compositions demonstrate a significant benefit over other clinically approved sealants. Although the disclosed polymer sealants may be utilized in combination with other sealants or devices, the studies herein indicate that their use alone is sufficient for most applications.

In mouse studies comparing suture only and suture plus supplemental blow spun sealant, marked differences were observed in survival (FIG. 23). In contrast, prior published mouse experiments using only clinically approved sealants showed no benefit over control (Slieker J. C. et al. (2013) "Prevention of leakage by sealing colon anastomosis: experimental study in a mouse model," J. Surg. Res. 184: 819-24). With regard to cytotoxicity in in vivo experimentation, both intramuscular and anastomosis specific biocompatibility in adherence to ISO standard 10993-6 with additional flow cytometry to quantify elevations in inflammatory cell populations evaluates any such potential site specific differences in biologic response (Oliva N. et al. (2015) "Regulation of dendrimer/dextran material performance by altered tissue microenvironment in inflammation and neoplasia," Science Translational Medicine 7:272ral 1). However, cytotoxicity was not observed, which is consistent with the in vitro cell viability data (FIGS. 15 and 16).

The blow spun polymer fiber sealants of the present invention exhibit substantially improved material properties as compared to conventional medical sealants. In addition, disclosed methods allow for direct polymer fiber generation and conformal application onto any surface, small or large. The disclosed solutions comprising blends of PLGA and PEG are ideal platforms for generating medical sealant, having the attributes of biocompatibility and degradability. Modulating hydrophilicity and adhesive strength is readily accomplished by varying the molecular weight and polymer blend of the composition and/or through chemical functionalization techniques. In addition, tuning the glass transition temperature of PLGA and melting temperature of PEG results in PLGA/PEG polymer blends that soften at body temperature (~37° C.), resulting in stronger adherence to tissue. Thus, the disclosed compositions and methods have significant impact on a wide array of surgical applications (e.g., such as aero-digestive and vascular procedures, visceral organ resections, wound dressings, and tissue reconstruction and engineering scaffolds) as well as on biomaterials fabrication techniques.

All publications mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A biocompatible composition comprising:
   (A) a first solution of between about 1% and about 20% weight per volume (w/v) poly(lactic-co-glycolic acid) (PLGA) having a weight average molecular weight of between about 50 kDa and about 200 kDa;
   (B) a second solution of between about 1% and about 20% w/v PLGA having a weight average molecular weight of between about 5 kDa and about 15 kDa; and
   (C) a third solution of between about 1% and about 20% w/v poly(ethylene glycol) (PEG).

2. The composition of claim 1, wherein said first solution or said second solution comprises between about 3% and about 15% w/v PLGA.

3. The composition of claim 1, wherein said third solution comprises between about 1% and about 10% w/v PEG.

4. The composition of claim 1, wherein each of said first solution and said second solution comprises between about 3% and about 10% w/v PLGA and said third solution comprises between about 1% and about 5% w/v PEG.

5. The composition of claim 1, wherein said solution of said PEG has a weight average molecular weight of between about 1 kDa and about 10 kDa.

6. The composition of claim 1, further comprising a volatile solvent.

7. The composition of claim 6, wherein said volatile solvent is acetone or ethyl acetate.

8. The composition of 1, wherein at least one of said PLGA or said PEG is modified to contain a therapeutic agent.

9. The composition of claim 8, wherein said therapeutic agent is selected from the group consisting of a protein, a peptide, an amine, an aliphatic compound, and an antibiotic.

10. A biocompatible polymer fiber construct comprising blow spun polymer fibers formed from a composition comprising:
    (A) a first solution of between about 1% and about 20% weight per volume (w/v) poly(lactic-co-glycolic acid) (PLGA) having a weight average molecular weight of between about 50 kDa and about 200 kDa;
    (B) a second solution of between about 1% and about 20% w/v PLGA having a weight average molecular weight of between about 5 kDa and about 15 kDa; and
    (C) a third solution of between about 1% and about 20% w/v poly(ethylene glycol) (PEG).

11. The construct of claim 10, wherein said first solution or said second solution comprises between about 3% and about 15% w/v PLGA.

12. The construct of claim 10, wherein said third solution comprises between about 1% and about 10% w/v PEG.

13. The construct of claim 10, wherein each of said first solution and said second solution comprises between about 3% and about 10% w/v PLGA and said third solution comprises between about 1% and about 5% w/v PEG.

14. The construct of claim 10, which is a tissue sealant, adhesive, hemostatic or scaffolding material.

15. The construct of claim 10, wherein said polymer fibers have an average diameter of less than about 500 nanometers.

16. A method of forming a polymer fiber construct, comprising:
    forming a plurality of polymer fibers using a solution blow spinning process, wherein said polymer fibers are formed from a composition comprising: i) a first solution of between about 1% and about 20% weight per volume (w/v) poly(lactic-co-glycolic acid) (PLGA) having a weight average molecular weight of between about 50 kDa and about 200 kDa; ii) a second solution of between about 1% and about 20% w/v PLGA having a weight average molecular weight of between about 5 kDa and about 15 kDa; and iii) a third solution of between about 1% and about 20% w/v poly(ethylene glycol) (PEG); and
    depositing said plurality of blow spun polymer fibers onto a target to form a conformal polymer fiber construct thereon.

17. The method of claim 16, wherein said target is a tissue surface, said polymer fiber construct formed on said tissue surface in vivo.

18. The method of claim 16, wherein said first solution or said second solution comprises between about 3% and about 15% w/v PLGA.

19. The method of claim 16, wherein said third solution comprises between about 1% and about 10% w/v PEG.

20. The method of claim 16, wherein each of said first solution and said second solution comprises between about 3% and about 10% w/v PLGA and said third solution comprises between about 1% and about 5% w/v PEG.

21. A biocompatible polymer fiber construct comprising blow spun polymer fibers formed from a solution comprising:
    (A) between about 1% and about 20% weight per volume (w/v) poly(lactic-co-glycolic acid) (PLGA) having a weight average molecular weight of between about 50 kDa and about 200 kDa;
    (B) between about 1% and about 20% w/v PLGA having a weight average molecular weight of between about 5 kDa and about 15 kDa; and
    (C) between about 1% and about 20% w/v poly(ethylene glycol) (PEG).

22. The construct of claim 21, wherein said solution comprises between about 3% and about 10% w/v PLGA having a weight average molecular weight of between about 50kDa and about 200 kDa, and between about 3% and about 10% w/v PLGA having a weight average molecular weight of between about 5 kDa and about 15 kDa.

23. The construct of claim 22, wherein said solution comprises between about 1% and about 5% w/v PEG.

24. The construct of claim 21, which is a tissue sealant, adhesive, hemostatic or scaffolding material.

25. A method of forming a polymer fiber construct, comprising:
    forming a plurality of polymer fibers using a solution blow spinning process, wherein said polymer fibers are formed from a solution comprising: i) between about 1% and about 20% weight per volume (w/v) poly(lactic-co-glycolic acid) (PLGA) having a weight average molecular weight of between about 50 kDa and about 200 kDa; ii) between about 1% and about 20% w/v PLGA having a weight average molecular weight of between about 5 kDa and about 15 kDa; and iii) between about 1% and about 20% w/v poly(ethylene glycol) (PEG); and
    depositing said plurality of blow spun polymer fibers onto a target to form a conformal polymer fiber construct thereon.

26. The method of claim 25, wherein said target is a tissue surface, said polymer fiber construct formed on said tissue surface in vivo.

27. The method of claim 25, wherein said solution comprises between about 3% and about 10% w/v PLGA having a weight average molecular weight of between about 50kDa and about 200 kDa, and between about 3% and about 10% w/v PLGA having a weight average molecular weight of between about 5 kDa and about 15 kDa.

28. The method of claim 27, wherein said solution comprises between about 1% and about 5% w/v PEG.

* * * * *